United States Patent
Crow et al.

(10) Patent No.: US 12,060,563 B2
(45) Date of Patent: Aug. 13, 2024

(54) PLANT REGULATORY ELEMENTS AND METHODS OF USE THEREOF

(71) Applicants: PIONEER HI-BRED INTERNATIONAL, INC., Johnston, IA (US); E. I. DU PONT DE NEMOURS AND COMPANY, Wilmington, DE (US)

(72) Inventors: Andrew Carl Crow, Grimes, IA (US); Scott Henry Diehn, West Des Moines, IA (US); Albert Laurence Lu, West Des Moines, IA (US); Carl Robert Simmons, Des Moines, IA (US); Lynne Eileen Sims, Polk City, IA (US)

(73) Assignee: PIONEER HI-BRED INTERNATIONAL, INC., IA (US)

( * ) Notice: Subject to any disclaimer, the term of this patent is extended or adjusted under 35 U.S.C. 154(b) by 162 days.

(21) Appl. No.: 17/218,737

(22) Filed: Mar. 31, 2021

(65) Prior Publication Data
US 2021/0230618 A1    Jul. 29, 2021

Related U.S. Application Data

(62) Division of application No. 15/778,542, filed as application No. PCT/US2016/063329 on Nov. 22, 2016, now Pat. No. 10,995,339.

(60) Provisional application No. 62/260,819, filed on Nov. 30, 2015.

(51) Int. Cl.
*C12N 15/82*    (2006.01)

(52) U.S. Cl.
CPC ..... *C12N 15/8216* (2013.01); *C12N 15/8223* (2013.01)

(58) Field of Classification Search
None
See application file for complete search history.

(56) References Cited

U.S. PATENT DOCUMENTS

| | | | |
|---|---|---|---|
| 6,392,121 B1 | 5/2002 | Mason et al. | |
| 6,420,547 B1 | 7/2002 | Maiti et al. | |
| 6,555,673 B1* | 4/2003 | Bowen et al. | C12N 15/8279 435/6.13 |
| 7,557,203 B2* | 7/2009 | Linemann et al. | C12N 15/8216 800/278 |
| 7,572,950 B2 | 8/2009 | Herbers et al. | |
| 10,995,339 B2* | 5/2021 | Crow | C12N 15/8242 |
| 2005/0108793 A1* | 5/2005 | Hu et al. | C07K 14/415 435/468 |
| 2013/0295609 A1 | 11/2013 | D'Aoust | |
| 2014/0059718 A1* | 2/2014 | Campanoni | C12N 15/8205 800/294 |
| 2017/0016021 A1 | 1/2017 | Yeh | |
| 2019/0194676 A1 | 6/2019 | Crow | |

FOREIGN PATENT DOCUMENTS

| | | |
|---|---|---|
| CN | 103740715 A | 4/2014 |
| WO | WO 01/44457 A2 * | 6/2001 |
| WO | WO 2010/069950 A1 * | 6/2010 |
| WO | 2010123904 A1 | 10/2010 |
| WO | 2012030711 A1 | 3/2012 |
| WO | 2012/058762 A1 | 5/2012 |
| WO | 2012/098111 A1 | 7/2012 |
| WO | 2012/098119 A2 | 7/2012 |
| WO | 2014/164775 A1 | 10/2014 |

OTHER PUBLICATIONS

Nitz et al. (2001) Plant Sci 161 :337-46.*
Cho & Cosgrove (2002) Plant Cell 14:3237-53.*
Hefferon, Kathleen L., et al.: "Multi-tasking of nonstructural gene products is required for bean yellow dwarf geminivirus transcriptional regulation", FEBS Journal, Oct. 2006 (Oct. 2006), vol. 273, No. 19, pp. 4482-4494.
Zhong, Huang, et al.: "A DNA replicon system for rapid high-level production of virus-like particles in plants", Biotechnology and Bioengineering, Jul. 1, 2009 (Jul. 1, 2009), vol. 103, No. 4, pp. 706-714.
International Search Report and Written Opinion, International Application No. PCT/US2016/063329 dated Mar. 31, 2017.
Idris A.M., et al., "Hollyhock Leaf Crumple Virus-[Cairo] Isolate HLCrV Hollyhock Segment A, Complete GenomeGenBank: AY036009.1," GenBank.
International Preliminary Report on Patentability for International Application No. PCT/US2016/063329, mailed Jun. 14, 2018, 12 Pages.

* cited by examiner

Primary Examiner — Russell T Boggs

(57) ABSTRACT

The present disclosure relates to the field of plant molecular biology, more particularly to regulation of gene expression in plants.

18 Claims, 3 Drawing Sheets

Specification includes a Sequence Listing.

Figure 1

MMV Enhancer:

ccactaaacattgctttgtcaaagctaaaaagatgatgcccg
acagccacttgtgtgaagcatgagagtccgtcccactaaga
aaattagtgaagcatcttccagtggtccctccactcacagctcaatc
agtgagcaacaggacgaaggaaatgacgtaagccatgacgtcta
atccca

Figure 2

2x MMV Enhancer:

ccactaaaacattgctttgtcaaaagctaaaaaagatgatgcccgacag
ccacttgtgtgaagcatgagaagccggtccctccactaagaaaattagt
gaagcatcttccagtggtccctccactcacagctcaatcagtgagcaac
aggacgaaggaaatgacgtaagccatgacgtctaatcccact<u>cgatcg</u>
acccactaaaacattgctttgtcaaaagctaaaaaagatgatgcccgac
agccacttgtgtgaagcatgagaagccggtccctccactaagaaaatta
gtgaagcatcttccagtggtccctccactcacagctcaatcagtgagcaa
caggacgaaggaaatgacgtaagccatgacgtctaatccca

Figure 3

3x MMV Enhancer:

ccactaaaacattgctttgtcaaagctaaaaagatgatgcccgacagccact
tgtgttgaagcatgagaagcccgtccctcactaagaaattagtgaagcatcttc
cagtggtccctccactcacagctcaatcagtgagcaacaggacgaaggaaatg
acgtaagccatgacgtctaatcccactcgagccactaaaacattgctttgtcaaa
agctaaaaagatgatgcccgacagccactgtgttgaagcatgagaagccggt
ccctccactaagaaattagtgaagcatcttccagtggtccctccactcacagctc
aatcagtgagcaacaggacgaaggaaatgacgtaagccatgacgtctaatccc
agtcgacccactaaaacattgctttgtcaaagctaaaaagatgatgcccgac
agccacttgtgtgaagcatgagaagccgtccctccactcacagctaagaaattagtgaa
gcatcttccagtggtccctccactcacagctcaatcagtgagcaacaggacgaa
ggaaatgacgtaagccatgacgtctaatccca

PLANT REGULATORY ELEMENTS AND METHODS OF USE THEREOF

CROSS-REFERENCE TO RELATED APPLICATIONS

This application claims the benefit of International Application Number PCT/US2016/063329 filed Nov. 22, 2016, which claims the benefit of U.S. Provisional Application No. 62/260,819, filed Nov. 30, 2015, which is hereby incorporated herein in its entirety by reference.

REFERENCE TO SEQUENCE LISTING SUBMITTED ELECTRONICALLY

A sequence listing having the file name "5307_WOPCT_SeqList.TXT" created on Dec. 22, 2015, and having a size of 6.87 kilobytes is filed in computer readable form concurrently with the specification. The sequence listing is part of the specification and is herein incorporated by reference in its entirety.

FIELD

The present disclosure relates to the field of plant molecular biology, more particularly to regulation of gene expression in plants.

BACKGROUND

Expression of heterologous DNA sequences in a plant host is dependent upon the presence of operably linked regulatory elements that are functional within the plant host. Choice of promoter sequence may determine when and where within the organism the heterologous DNA sequence is expressed. Where expression in specific tissues or organs is desired, tissue-preferred promoters may be used. Where gene expression in response to a stimulus is desired, inducible promoters are the regulatory element of choice. In contrast, where continuous expression is desired throughout the cells of a plant, constitutive promoters are utilized. Additional regulatory sequences upstream and/or downstream from the core promoter sequence may be included in the expression constructs of transformation vectors to bring about varying levels of expression of heterologous nucleotide sequences in a transgenic plant.

Frequently it is desirable to express a DNA sequence in particular tissues or organs of a plant. For example, increased resistance of a plant to infection by soil- and air-borne pathogens might be accomplished by genetic manipulation of the plant's genome to comprise a tissue-preferred promoter operably linked to a heterologous pathogen-resistance gene such that pathogen-resistance proteins are produced in the desired plant tissue. Alternatively, it might be desirable to inhibit expression of a native DNA sequence within a plant's tissues to achieve a desired phenotype. In this case, such inhibition might be accomplished with transformation of the plant to comprise a tissue-preferred promoter operably linked to an antisense nucleotide sequence, such that expression of the antisense sequence produces an RNA transcript that interferes with translation of the mRNA of the native DNA sequence.

Genetically altering plants through the use of genetic engineering techniques and thus producing a plant with useful traits requires the availability of a variety of regulatory elements. An accumulation of promoters and other regulatory elements would enable the investigator to express at desired levels and cellular locales recombinant DNA molecules. Therefore, a collection of constitutive promoters would allow for a new trait to be expressed at the desired level in the desired tissue. Thus, isolation and characterization of constitutive regulatory elements that may serve as regulatory regions for expression of heterologous nucleotide sequences of interest in a measured constitutive manner are needed for genetic manipulation of plants.

Isolation and characterization of geminiviral regulatory elements, particularly promoters that can serve as regulatory elements for constitutive expression of isolated nucleotide sequences of interest, are needed for impacting various traits in plants and for use with scorable markers.

BRIEF SUMMARY

Compositions and methods for regulating expression of a heterologous nucleotide sequence of interest in a plant or plant cell are provided. DNA molecules comprising novel nucleotide sequences for regulatory elements that initiate transcription are provided. In some embodiments the regulatory element has promoter activity initiating transcription in the plant cell. Certain embodiments comprise the nucleotide sequences set forth in SEQ ID NOs: 1-13. Also included are functional fragments or variants of the sequences set forth in SEQ ID NOs: 4-13 wherein said sequences initiate transcription in a plant cell, and a polynucleotide sequence comprising a sequence having at least 85% sequence identity to the sequences set forth in SEQ ID NOs: 4-13, wherein said sequences initiate transcription in the plant cell. Embodiments also include DNA constructs comprising a promoter operably linked to a heterologous nucleotide sequence of interest, wherein said promoter is capable of driving expression of said heterologous nucleotide sequence in a plant cell and said promoter comprises one of the nucleotide sequences disclosed herein. Also included are enhancer elements of the sequence set forth in SEQ ID NOs: 1-3. Embodiments also include DNA constructs comprising an enhancer and a heterologous promoter operably linked to a heterologous polynucleotide sequence of interest, wherein said enhancer and heterologous promoter is capable of driving expression of said polynucleotide sequence in a plant cell and said enhancer and heterologous promoter each comprises one of the polynucleotide sequences set forth in SEQ ID NOs: 1-14. Embodiments further provide expression vectors, and plants or plant cells having stably incorporated into their genomes a DNA construct as is described above. Additionally, compositions include transgenic seed of such plants.

Further embodiments comprise a means for selectively expressing a polynucleotide sequence in a plant, comprising transforming a plant cell with a DNA construct, and regenerating a transformed plant from said plant cell, said DNA construct comprising a promoter of SEQ ID NOs: 4-13 and a heterologous polynucleotide sequence operably linked to said promoter, wherein said promoter initiates transcription of said polynucleotide sequence in the regenerated plant. In this manner, the promoter sequences are useful for controlling the expression of operably linked coding sequences in a tissue-preferred manner. In another embodiment, the DNA construct further comprises a heterologous enhancer element.

Downstream from the transcriptional initiation region of the regulatory element will be a sequence of interest that will provide for modification of the phenotype of the plant. Such modification includes modulating the production of an endogenous product as to amount, relative distribution, or the like, or production of an exogenous expression product, to provide for a novel or modulated function or product in the plant. For example, a heterologous polynucleotide sequence that encodes a gene product that confers resistance or tolerance to herbicide, salt, cold, drought, pathogen, nematodes or insects is encompassed.

In a further embodiment, a method for modulating expression of a gene in a stably transformed plant is provided, comprising the steps of (a) transforming a plant cell with a DNA construct comprising the promoter disclosed herein operably linked to at least one heterologous polynucleotide sequence; (b) growing the plant cell under plant growing conditions and (c) regenerating a stably transformed plant from the plant cell wherein expression of the linked nucleotide sequence alters the phenotype of the plant. In another embodiment, the DNA construct further comprises a heterologous enhancer element.

Expression cassettes comprising the regulatory element sequences of SEQ ID NOs: 1-13 operably linked to a heterologous nucleotide sequence of interest are provided. Additionally provided are transformed plant cells, plant tissues, seeds, and plants.

DETAILED DESCRIPTION OF THE FIGURES

FIG. 1. The MMV enhancer sequence (SEQ ID NO: 1).

FIG. 2. The 2×MMV enhancer version (SEQ ID NO:2) was created from the 3× version (SEQ ID NO:3) by cutting the XhoI and SalI sites then filling them in and ligating, which created a PvuI site with a couple of extra bases between the two sequences (underlined).

FIG. 3. The 3×MMV enhancer version (SEQ ID NO:3) was created by assembling three copies of the MMV enhancer sequence with an XhoI site between the first and second MMV segment and a SalI site between the second and third MMV segment. For cloning purposes, NotI and PspMOI sites were added to the 5 prime and 3 prime ends of the sequence, respectively (underlined).

DETAILED DESCRIPTION

The article "a" and "an" are used herein to refer to one or more than one (i.e., to at least one) of the grammatical object of the article. By way of example, "an element" means one or more element.

The disclosure relates to compositions and methods drawn to plant regulatory elements and methods of their use. The compositions comprise nucleotide sequences for the regulatory region of Bean Yellow Dwarf Virus (BYDV), Beet Mild Curly Top Virus (BMTV), East African Cassava Mosaic (Cameroon) Virus (EACMCV), Hollyhock leaf crumple virus (HLCV), Horseradish Curly Top Virus (HCTV), Mirabilis Mosaic Virus (MMV), Macroptilium Yellow Mosaic Florida Virus (MYMFV), Sugarcane Streak (Egypt) Virus (SSEV), Sugarcane Streak Virus (SSV), Tomato Curly Stunt Virus (South Africa) (TCSVSA), and Wheat Dwarf Virus (WDWV). The compositions further comprise DNA constructs comprising at least one polynucleotide sequence for the regulatory region of any BYDV, BMTV, EACMCV, HLCV, HCTV, MMV, MYMFV, SSEV, SSV, TCSVSA, and WDWV operably linked to a heterologous polynucleotide sequence of interest. In particular, isolated nucleic acid molecules comprising the polynucleotide sequences set forth in SEQ ID NOs: 1-13, and fragments, variants and complements thereof are provided.

TABLE 1

| SEQ ID NO: | ORGANISM | POLYNUCLEOTIDE/ POLYPEPTIDE | DESCRIPTION |
| --- | --- | --- | --- |
| 1 | MMV | polynucleotide | Full Length |
| 2 | Synthetic | polynucleotide | Duplicate (2×) |
| 3 | Synthetic | polynucleotide | Triplicate (3×) |
| 4 | BYDV | polynucleotide | Full Length |
| 5 | BMTV | polynucleotide | Full Length |
| 6 | EACMCV | polynucleotide | Full Length |
| 7 | HLCV | polynucleotide | Full Length |
| 8 | HCTV | polynucleotide | Full Length |
| 9 | MYMFV | polynucleotide | Full Length |
| 10 | SSEV | polynucleotide | Full Length |
| 11 | SSV | polynucleotide | Full Length |
| 12 | TCSVSA | polynucleotide | Full Length |
| 13 | WDWV | polynucleotide | Full Length |

The geminiviral regulatory element sequences, SEQ ID NOs: 1-13, include polynucleotide constructs that allow initiation of transcription in a plant. In specific embodiments, a geminiviral regulatory element allows initiation of transcription in a constitutive manner. Such constructs may comprise regulated transcription initiation regions associated with plant developmental regulation. Thus, the compositions disclosed herein may include DNA constructs comprising a nucleotide sequence of interest operably linked to a plant promoter, particularly a constitutive promoter sequence, more particularly a geminiviral promoter and intron sequence. In another preferred embodiment, the DNA construct further comprises a heterologous enhancer element. In one embodiment, a heterologous enhancer element comprises SEQ ID NOs: 1-3. Geminiviral regulatory region sequences are set forth in SEQ ID NOs: 1-13.

Compositions may include the nucleotide sequences for the geminiviral regulatory elements, fragments and variants thereof. In specific embodiments, the regulatory element sequences disclosed herein are useful for expressing sequences of interest in a constitutive manner. The nucleotide sequences may also find use in the construction of expression vectors for subsequent expression of a heterologous nucleotide sequence in a plant of interest or as probes for the isolation of other geminiviral-like regulatory elements. One embodiment is provided for DNA constructs comprising a geminiviral regulatory element nucleotide sequences set forth in SEQ ID NOs: 4-13 or a plant based regulatory element as set forth in SEQ ID NO: 14, and a heterologous enhancer elements set forth in SEQ ID NOs: 1-3, operably linked to a heterologous polynucleotide sequence of interest, and any combinations thereof.

Regulatory Elements

The term "regulatory element" refers to a nucleic acid molecule having gene regulatory activity, i.e. one that has the ability to affect the transcription and/or translation of an operably linked transcribable polynucleotide molecule. The term "gene regulatory activity" thus refers to the ability to affect the expression of an operably linked transcribable polynucleotide molecule by affecting the transcription and/or translation of that operably linked transcribable polynucleotide molecule. Gene regulatory activity may be positive and/or negative and the effect may be characterized by its temporal, spatial, developmental, tissue, environmental, physiological, pathological, cell cycle, and/or chemically responsive qualities as well as by quantitative or qualitative indications.

Regulatory elements such as promoters, enhancers, leaders, introns, and transcription termination regions are nucleic acid molecules that have gene regulatory activity and play an integral part in the overall expression of genes in living cells. Isolated regulatory elements, such as promoters and leaders that function in plants are therefore useful for modifying plant phenotypes through the methods of genetic engineering. A promoter is useful as a regulatory element for modulating the expression of an operably linked transcribable polynucleotide molecule.

As used herein, a "gene expression pattern" is any pattern of transcription of an operably linked nucleic acid molecule into a transcribed RNA molecule. Expression may be characterized by its temporal, spatial, developmental, tissue, environmental, physiological, pathological, cell cycle, and/or chemically responsive qualities as well as by quantitative or qualitative indications. The transcribed RNA molecule may be translated to produce a protein molecule or may provide an antisense or other regulatory RNA molecule, such as a dsRNA, a tRNA, an rRNA, a miRNA, and the like.

The regulatory element sequences or variants or fragments thereof, when operably linked to a heterologous nucleotide sequence of interest can drive constitutive expression of the heterologous polynucleotide sequence in the tissue of the plant expressing this construct. The term "constitutive expression," means that expression of the heterologous nucleotide sequence is found throughout the plant or in a majority of tissues of the plant.

As used herein, the term "protein expression" is any pattern of translation of a transcribed RNA molecule into a protein molecule. Protein expression may be characterized by its temporal, spatial, developmental, or morphological qualities as well as by quantitative or qualitative indications.

As used herein, the term "promoter" refers generally to a nucleic acid molecule that is involved in recognition and binding of RNA polymerase II and other proteins (trans-acting transcription factors) to initiate transcription. A promoter may be initially isolated from the 5' untranslated region (5' UTR) of a genomic copy of a gene. Alternately, promoters may be synthetically produced or manipulated DNA molecules. Promoters may also be chimeric, that is a promoter produced through the fusion of two or more heterologous DNA molecules.

In one embodiment, fragments are provided of a promoter sequence disclosed herein. Promoter fragments may exhibit promoter activity, and may be useful alone or in combination with other promoters and promoter fragments, such as in constructing chimeric promoters. In specific embodiments, fragments of a promoter are provided comprising at least about 50, 95, 150, 250, 500, or about 750 contiguous nucleotides of a polynucleotide molecule having promoter activity disclosed herein. Such fragments may exhibit at least about 85 percent, about 90 percent, about 95 percent, about 98 percent, or about 99 percent, or greater, identity with a reference sequence when optimally aligned to the reference sequence.

A promoter or promoter fragment may also be analyzed for the presence of known promoter elements, i.e. DNA sequence characteristics, such as a TATA-box and other known transcription factor binding site motifs. Identification of such known promoter elements may be used by one of skill in the art to design variants of the promoter having a similar expression pattern to the original promoter.

As used herein, the term "enhancer" or "enhancer element" refers to a cis-acting transcriptional regulatory element, a.k.a. cis-element, which confers an aspect of the overall expression pattern, but is usually insufficient alone to drive transcription, of an operably linked polynucleotide sequence. Unlike promoters, enhancer elements do not usually include a transcription start site (TSS) or TATA box. A promoter may naturally comprise one or more enhancer elements that affect the transcription of an operably linked polynucleotide sequence. An isolated enhancer element may also be fused to a heterologous promoter to produce a heterologous chimeric promoter cis-element, which confers an aspect of the overall modulation of gene expression. A promoter or promoter fragment disclosed herein may comprise one or more enhancer elements that effect the transcription of operably linked genes. Many enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements may be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis using known cis-element motifs or enhancer elements as a target sequence or target motif with conventional DNA sequence comparison methods, such as BLAST. The fine structure of an enhancer domain may be further studied by mutagenesis (or substitution) of one or more nucleotides or by other conventional methods Enhancer elements may be obtained by chemical synthesis or by isolation from regulatory elements that include such elements, and they may be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable polynucleotide molecules are encompassed.

As used herein, the term "5' untranslated flanking region" refers to a DNA molecule isolated from the untranslated 5' region (5' UTR) of a genomic copy of a gene and defined generally as a nucleotide segment between the transcription start site (TSS) and the protein coding sequence start site. These sequences, or leaders, may be synthetically produced or manipulated DNA elements. A leader may be used as a 5' regulatory element for modulating expression of an operably linked transcribable polynucleotide molecule. Leader molecules may be used with a heterologous promoter or with their native promoter. Promoter molecules may thus be operably linked to their native leader or may be operably linked to a heterologous leader.

As used herein, the term "chimeric" refers to a single DNA molecule produced by fusing a first DNA molecule to a second DNA molecule, where neither first nor second DNA molecule would normally be found in that configuration, i.e. fused to the other. The chimeric DNA molecule is thus a new DNA molecule not otherwise normally found in nature. As used herein, the term "chimeric promoter" refers to a promoter produced through such manipulation of DNA molecules. A chimeric promoter may combine two or more DNA fragments; an example would be the fusion of a promoter to a heterologous enhancer element. Thus, the design, construction, and use of chimeric promoters according to the methods disclosed herein for modulating the expression of operably linked transcribable polynucleotide molecules are encompassed.

In one embodiment, the nucleotide sequences disclosed herein, located within introns, or 3' of the coding region sequence may also contribute to the regulation of expression of a coding region of interest. Examples of suitable introns include, but are not limited to, the maize IVS6 intron, or the maize actin intron. A regulatory element may also include those elements located downstream (3') to the site of transcription initiation, or within transcribed regions, or both. A post-transcriptional regulatory element may include elements that are active following transcription initiation, for example translational and transcriptional enhancers, translational and transcriptional repressors, and mRNA stability determinants.

The regulatory elements, or variants or fragments thereof, may be operatively associated with one or more heterologous regulatory elements in order to modulate the activity of the heterologous regulatory element. Such modulation includes enhancing or repressing transcriptional activity of the heterologous regulatory element, modulating post-transcriptional events, or either enhancing or repressing transcriptional activity of the heterologous regulatory element and modulating post-transcriptional events. For example, one or more regulatory elements, or fragments thereof, may be operatively associated with constitutive, inducible, or tissue specific promoters or fragment thereof, to modulate the activity of such promoters within desired tissues in plant cells.

The composition may encompasses isolated or recombinant nucleic acid. An "isolated" or "recombinant" nucleic acid molecule (or DNA) is used herein to refer to a nucleic acid sequence (or DNA) that is no longer in its natural environment, for example in an in vitro or in a heterologous recombinant bacterial or plant host cell. An isolated or recombinant nucleic acid molecule, or biologically active portion thereof, is substantially free of other cellular material or culture medium when produced by recombinant techniques, or substantially free of chemical precursors or other chemicals when chemically synthesized. An isolated or recombinant nucleic acid is free of sequences (optimally protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule may contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. The geminiviral regulatory element sequences disclosed herein may be isolated from the 5' untranslated region flanking their respective transcription initiation sites. As used herein, the terms "polynucleotide" and "nucleotide" are both intended to mean one or more nucleotide and may be used interchangeably in the singular or plural.

The compositions may encompasses isolated or substantially purified nucleic acid compositions. An "isolated" or "purified" nucleic acid molecule or biologically active portion thereof is substantially free of other cellular material or culture medium when produced by recombinant techniques or substantially free of chemical precursors or other chemicals when chemically synthesized. An "isolated" nucleic acid is substantially free of sequences (including protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule may contain less than about 5 kb, 4 kb, 3 kb, 2 kb, 1 kb, 0.5 kb or 0.1 kb of nucleotide sequences that naturally flank the nucleic acid molecule in genomic DNA of the cell from which the nucleic acid is derived. The geminiviral sequences disclosed herein may be isolated from the 5' untranslated region flanking their respective transcription initiation sites.

Fragments and variants of the disclosed regulatory element nucleotide sequences are also encompassed by the present disclosure. As used herein, the term "fragment" refers to a portion of the nucleic acid sequence. Fragments of geminiviral regulatory sequences may retain the biological activity of initiating transcription, more particularly driving transcription in a constitutive manner. Alternatively, fragments of a nucleotide sequence that are useful as hybridization probes may not necessarily retain biological activity. Fragments of a nucleotide sequence for the geminiviral regulatory region may range from at least about 20 nucleotides, about 50 nucleotides, about 100 nucleotides, and up to the full length of SEQ ID NOs: 1-13.

A biologically active portion of a geminiviral regulatory element may be prepared by isolating a portion of the geminiviral promoter sequence of the disclosure, and assessing the promoter activity of the portion. Nucleic acid molecules that are fragments of a geminiviral regulatory polynucleotide sequence comprise at least about 16, 50, 75, 100, 150, 200, 250, 300, 350, 400, 450, 500, 550, 600, 650, 700 or 800 nucleotides or up to the number of nucleotides present in a full-length geminiviral regulatory sequence disclosed herein.

For nucleotide sequences, a variant comprises a deletion and/or addition of one or more nucleotides at one or more internal sites within the native polynucleotide sequence and/or a substitution of one or more nucleotides at one or more sites in the native polynucleotide. For nucleotide sequences, variants may be identified with the use of well-known molecular biology techniques, as, for example, with polymerase chain reaction (PCR) and hybridization techniques as outlined below. Variant nucleotide sequences may include synthetically derived nucleotide sequences, such as those generated, for example, by using site-directed mutagenesis. Generally, variants of a particular nucleotide sequence of the disclosure will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular nucleotide sequence as determined by sequence alignment programs and parameters described elsewhere herein. A biologically active variant of a nucleotide sequence of the disclosure may differ from that sequence by as few as 1-15 nucleic acid residues, as few as 1-10, as few as 6-10, as few as 5, as few as 4, 3, 2, or even 1 nucleic acid residue. Variant nucleotide sequences also encompass sequences derived from a mutagenic and recombinogenic procedure such as DNA shuffling. With such a procedure, geminiviral regulatory element nucleotide sequences may be manipulated to create new geminiviral regulatory elements. In this manner, libraries of recombinant polynucleotides are generated from a population of related sequence polynucleotides comprising sequence regions that have substantial sequence identity and may be homologously recombined in vitro or in vivo. Strategies for such DNA shuffling are known in the art. See, for example, Stemmer (1994) Proc. Natl. Acad. Sci. USA 91:10747-10751; Stemmer (1994) Nature 370:389-391; Crameri et al. (1997) Nature Biotech. 15:436-438; Moore et al. (1997) J.

Mol. Biol. 272:336-347; Zhang et al. (1997) Proc. Natl. Acad. Sci. USA 94:4504-4509; Crameri et al. (1998) Nature 391:288-291; and U.S. Pat. Nos. 5,605,793 and 5,837,458.

The nucleotide sequences of the disclosure may be used to isolate corresponding sequences from other organisms, particularly other plants, more particularly other monocots. In this manner, methods such as PCR, hybridization and the like may be used to identify such sequences based on their sequence homology to the sequences set forth herein. Sequences isolated based on their sequence identity to the entire geminiviral sequences set forth herein or to fragments thereof are encompassed by the present disclosure.

In a PCR approach, oligonucleotide primers may be designed for use in PCR reactions to amplify corresponding DNA sequences from cDNA or genomic DNA extracted from any plant of interest. Methods for designing PCR primers and PCR cloning are generally known in the art and are disclosed in, Sambrook, supra. See also, Innis, et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York), herein incorporated by reference in their entirety. Known methods of PCR include, but are not limited to, methods using paired primers, nested primers, single specific primers, degenerate primers, gene-specific primers, vector-specific primers, partially-mismatched primers and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides and may be labeled with a detectable group such as $^{32}P$ or any other detectable marker. Thus, for example, probes for hybridization may be made by labeling synthetic oligonucleotides based on the geminiviral regulatory element sequences of the disclosure. Methods for preparation of probes for hybridization and for construction of genomic libraries are generally known in the art and are disclosed in Sambrook, supra.

For example, the entire geminiviral regulatory element sequence disclosed herein, or one or more portions thereof, may be used as a probe capable of specifically hybridizing to corresponding dicot geminiviral regulatory element sequences and messenger RNAs. To achieve specific hybridization under a variety of conditions, such probes include sequences that are unique among geminiviral regulatory element sequences and are generally at least about 10 nucleotides in length or at least about 20 nucleotides in length. Such probes may be used to amplify corresponding geminiviral regulatory element sequences from a chosen plant by PCR. This technique may be used to isolate additional coding sequences from a desired organism or as a diagnostic assay to determine the presence of coding sequences in an organism. Hybridization techniques include hybridization screening of plated DNA libraries (either plaques or colonies, see, for example, Sambrook, supra).

Hybridization of such sequences may be carried out under stringent conditions. The terms "stringent conditions" or "stringent hybridization conditions" are intended to mean conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions may be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C. and a wash in 1 times to 2 times SSC (20 times SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C. and a wash in 0.5 times to 1 times SSC at 55 to 60° C. Exemplary high stringency conditions include hybridization in 50% formamide, 1 M NaCl, 1% SDS at 37° C., and a final wash in 0.1 times SSC at 60 to 65° C. for a duration of at least 30 minutes. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the thermal melting point ($T_m$) can be approximated from the equation of Meinkoth and Wahl, (1984) *Anal. Biochem* 138:267 284: $T_m=81.5° C.+16.6$ (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching, thus, $T_m$, hybridization, and/or wash conditions can be adjusted to hybridize to sequences of the desired identity. For example, if sequences with 90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3 or 4° C. lower than the $T_m$; moderately stringent conditions can utilize a hybridization and/or wash at 6, 7, 8, 9 or 10° C. lower than the $T_m$; low stringency conditions can utilize a hybridization and/or wash at 11, 12, 13, 14, 15 or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen, (1993) Laboratory Techniques in Biochemistry and Molecular Biology—Hybridization with Nucleic Acid Probes, Part I, Chapter 2 (Elsevier, New York); and Ausubel, et al., eds. (1995) Current Protocols in Molecular Biology, Chapter 2 (Greene Publishing and Wiley-Interscience, New York), herein incorporated by reference in their entirety. See also, Sambrook.

Thus, isolated sequences that have constitutive promoter activity and which hybridize under stringent conditions to the geminiviral regulatory sequences disclosed herein or to fragments thereof, are encompassed by the present disclosure.

In general, sequences that have promoter activity and hybridize to the polynucleotide sequences disclosed herein will be at least 40% to 50% homologous, about 60%, 70%, 80%, 85%, 90%, 95% to 98% homologous or more with the disclosed sequences. That is, the sequence similarity of sequences may range, sharing at least about 40% to 50%, about 60% to 70%, and about 80%, 85%, 90%, 95% to 98% sequence similarity.

The following terms are used to describe the sequence relationships between two or more nucleic acids or polynucleotides: (a) "reference sequence", (b) "comparison window", (c) "sequence identity", (d) "percentage of sequence identity" and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller, (1988) *CABIOS* 4:11-17; the algorithm of Smith, et al., (1981) *Adv. Appl. Math.* 2:482; the algorithm of Needleman and Wunsch, (1970) *J. Mol. Biol.* 48:443-453; the algorithm of Pearson and Lipman, (1988) *Proc. Natl. Acad. Sci.* 85:2444-2448; the algorithm of Karlin and Altschul, (1990) *Proc. Natl. Acad. Sci. USA* 872:264, modified as in Karlin and Altschul, (1993) *Proc. Natl. Acad. Sci. USA* 90:5873-5877, herein incorporated by reference in their entirety.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA and TFASTA in the GCG Wisconsin Genetics Software Package®, Version 10 (available from Accelrys Inc., 9685 Scranton Road, San Diego, Calif., USA). Alignments using these programs can be performed using the default parameters. The CLUSTAL program is well described by Higgins, et al., (1988) *Gene* 73:237-244 (1988); Higgins, et al., (1989) *CABIOS* 5:151-153; Corpet, et al., (1988) *Nucleic Acids Res.* 16:10881-90; Huang, et al., (1992) *CABIOS* 8:155-65; and Pearson, et al., (1994) *Meth. Mol. Biol.* 24:307-331, herein incorporated by reference in their entirety. The ALIGN program is based on the algorithm of Myers and Miller, (1988) supra. A PAM120 weight residue table, a gap length penalty of 12, and a gap penalty of 4 can be used with the ALIGN program when comparing amino acid sequences. The BLAST programs of Altschul, et al., (1990) *J. Mol. Biol.* 215:403, herein incorporated by reference in its entirety, are based on the algorithm of Karlin and Altschul, (1990) supra. BLAST nucleotide searches can be performed with the BLASTN program, score=100, word length=12, to obtain nucleotide sequences homologous to a nucleotide sequence encoding a protein of the disclosure. BLAST protein searches can be performed with the BLASTX program, score=50, word length=3, to obtain amino acid sequences homologous to a protein or polypeptide of the disclosure. To obtain gapped alignments for comparison purposes, Gapped BLAST (in BLAST 2.0) can be utilized as described in Altschul, et al., (1997) *Nucleic Acids Res.* 25:3389, herein incorporated by reference in its entirety. Alternatively, PSI-BLAST (in BLAST 2.0) can be used to perform an iterated search that detects distant relationships between molecules. See, Altschul, et al., (1997) supra. When utilizing BLAST, Gapped BLAST, PSI-BLAST, the default parameters of the respective programs (e.g., BLASTN for nucleotide sequences, BLASTX for proteins) can be used. See, the web site for the National Center for Biotechnology Information on the World Wide Web at ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. As used herein, "equivalent program" is any sequence comparison program that, for any two sequences in question, generates an alignment having identical nucleotide or amino acid residue matches and an identical percent sequence identity when compared to the corresponding alignment generated by GAP Version 10.

The GAP program uses the algorithm of Needleman and Wunsch, supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package® for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package® is BLOSUM62 (see, Henikoff and Henikoff, (1989) *Proc. Natl. Acad. Sci. USA* 89:10915, herein incorporated by reference in its entirety).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) The term "substantial identity" of polynucleotide sequences means that a polynucleotide comprises a sequence that has at least 70% sequence identity, at least 80%, at least 90%, and at least 95%, compared to a reference sequence using one of the alignment programs described using standard parameters.

Another indication that nucleotide sequences are substantially identical is if two molecules hybridize to each other under stringent conditions. Generally, stringent conditions are selected to be about 5° C. lower than the $T_m$ for the specific sequence at a defined ionic strength and pH. However, stringent conditions encompass temperatures in the range of about 1° C. to about 20° C. lower than the $T_m$, depending upon the desired degree of stringency as otherwise qualified herein.

In one embodiment, enhancers set forth in SEQ ID NOs: 1-3 may be utilized in combination with the promoter sequences set forth in SEQ ID NOs: 4-13 Enhancers are nucleotide sequences that may act to increase the expression of a promoter region Enhancers include the SV40 enhancer region, the 35S enhancer element and the like. Some enhancers may also alter normal promoter expression patterns, for example, by causing a promoter to be expressed constitutively when without the enhancer, the same promoter is expressed only in one specific tissue or a few specific tissues.

Modifications of the isolated regulatory element sequences of the present disclosure may provide for a range of expression of the heterologous nucleotide sequence. Thus, they may be modified to be weak promoters or strong promoters. Generally, a "weak promoter" means a promoter that drives expression of a coding sequence at a low level. A "low level" of expression is intended to mean expression at levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts.

The geminiviral regulatory elements disclosed herein may be used to increase or decrease expression, thereby resulting in a change in phenotype of the transformed plant. The nucleotide sequences disclosed herein, as well as variants and fragments thereof, are useful in the genetic manipulation of any plant. The geminiviral regulatory element sequences are useful in this aspect when operably linked with a heterologous nucleotide sequence whose expression is to be controlled to achieve a desired phenotypic response. The term "operably linked" means that the transcription or translation of the heterologous nucleotide sequence is under the influence of the regulatory element sequence. In this manner, the regulatory element sequences disclosed herein may be provided in expression cassettes along with heterologous nucleotide sequences of interest for expression in the plant of interest, more particularly for expression in the reproductive tissue of the transformed plant.

The regulatory sequences of the embodiments are provided in DNA constructs for expression in the organism of interest. An "expression cassette" as used herein means a DNA construct comprising a regulatory sequence of the embodiments operably linked to a heterologous polynucleotide encoding a polypeptide of interest. Such expression cassettes will comprise a transcriptional initiation region comprising one of the regulatory element nucleotide sequences of the present disclosure, or variants or fragments thereof, operably linked to the heterologous nucleotide sequence. Such an expression cassette may be provided with a plurality of restriction sites for insertion of the nucleotide sequence to be under the transcriptional regulation of the regulatory regions. The expression cassette may additionally contain selectable marker genes as well as 3' termination regions.

The expression cassette may include, in the 5'-3' direction of transcription, a transcriptional initiation region (i.e., a promoter, or variant or fragment thereof, of the disclosure), a translational initiation region, a heterologous nucleotide sequence of interest, a translational termination region and optionally, a transcriptional termination region functional in the host organism. The regulatory regions (i.e., promoters, enhancers, transcriptional regulatory regions, and translational termination regions) and/or the polynucleotide of the embodiments may be native/analogous to the host cell or to each other. Alternatively, the regulatory regions and/or the polynucleotide of the embodiments may be heterologous to the host cell or to each other.

As used herein, "heterologous" in reference to a sequence is a sequence that originates from a foreign species or, if from the same species, is substantially modified from its native form in composition and/or genomic locus by deliberate human intervention. For example, a regulatory element operably linked to a heterologous polynucleotide is from a species different from the species from which the polynucleotide was derived or, if from the same/analogous species, one or both are substantially modified from their original form and/or genomic locus or the regulatory element is not the native regulatory element for the operably linked polynucleotide.

The termination region may be native with the transcriptional initiation region, may be native with the operably linked DNA sequence of interest, may be native with the plant host, or may be derived from another source (i.e., foreign or heterologous to the regulatory element, the DNA sequence being expressed, the plant host, or any combination thereof).

The geminiviral regulatory sequence disclosed herein, as well as variants and fragments thereof, are useful for genetic engineering of plants, e.g. for the production of a transformed or transgenic plant, to express a phenotype of interest. As used herein, the terms "transformed plant" and "transgenic plant" refer to a plant that comprises within its genome a heterologous polynucleotide. Generally, the heterologous polynucleotide is stably integrated within the genome of a transgenic or transformed plant such that the polynucleotide is passed on to successive generations. The heterologous polynucleotide may be integrated into the genome alone or as part of a recombinant DNA construct. It is to be understood that as used herein the term "transgenic" includes any cell, cell line, callus, tissue, plant part or plant the genotype of which has been altered by the presence of heterologous nucleic acid including those transgenics initially so altered as well as those created by sexual crosses or asexual propagation from the initial transgenic.

A transgenic "event" is produced by transformation of plant cells with a heterologous DNA construct, including a nucleic acid expression cassette that comprises a transgene of interest, the regeneration of a population of plants resulting from the insertion of the transgene into the genome of the plant and selection of a particular plant characterized by insertion into a particular genome location. An event is characterized phenotypically by the expression of the transgene. At the genetic level, an event is part of the genetic makeup of a plant. The term "event" also refers to progeny produced by a sexual cross between the transformant and another plant wherein the progeny include the heterologous DNA.

As used herein, the term plant includes whole plants, plant organs (e.g., leaves, stems, roots, etc.), plant cells, plant protoplasts, plant cell tissue cultures from which plants can be regenerated, plant calli, plant clumps and plant cells that are intact in plants or parts of plants such as embryos, pollen, ovules, seeds, leaves, flowers, branches, fruit, kernels, ears, cobs, husks, stalks, roots, root tips, anthers and the like. Grain is intended to mean the mature seed produced by commercial growers for purposes other than growing or reproducing the species. Progeny, variants and mutants of the regenerated plants are also included within the scope of the disclosure, provided that these parts comprise the introduced polynucleotides.

The present disclosure may be used for transformation of any plant species, including, but not limited to, monocots and dicots. Examples of plant species include corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (Citrus spp.), cocoa (*Theobroma cacao*), tea (*Camellia sinensis*), banana (*Musa* spp.), avocado (*Peryea americana*), fig (*Ficus casica*), guava (*Psidium guajava*), mango (*Mangifera indica*), olive (*Olea europaea*), papaya (*Carica papaya*), cashew (*Anacardium occidentale*), macadamia (Macadamia integrifolia), almond (*Prunus amygdalus*), sugar beets (*Beta vulgaris*), sugarcane (*Saccharum* spp.), oats, barley, vegetables, ornamentals and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.) and members of the genus *Cucumis* such as cucumber (*C. sativus*), cantaloupe (*C. cantalupensis*) and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*) and chrysanthemum.

Conifers that may be employed in practicing the present disclosure include, for example, pines such as loblolly pine (*Pinus taeda*), slash pine (*Pinus elliotii*), ponderosa pine (*Pinusponderosa*), lodgepole pine (*Pinus contorta*) and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*) and cedars such as Western red cedar (*Thuja plicata*) and Alaska yellow-cedar (*Chamaecyparis nootkatensis*). In specific embodiments, plants of the present disclosure are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Heterologous coding sequences expressed by a geminiviral regulatory element sequence of the disclosure may be used for varying the phenotype of a plant. Various changes in phenotype are of interest including modifying expression of a gene in a plant, altering a plant's pathogen or insect defense mechanism, increasing a plant's tolerance to herbicides, altering plant development to respond to environmental stress, modulating the plant's response to salt, temperature (hot and cold), drought and the like. These results may be achieved by the expression of a heterologous nucleotide sequence of interest comprising an appropriate gene product. In specific embodiments, the heterologous nucleotide sequence of interest is an endogenous plant sequence whose expression level is increased in the plant or plant part. Results may be achieved by providing for altered expression of one or more endogenous gene products, particularly hormones, receptors, signaling molecules, enzymes, transporters or cofactors or by affecting nutrient uptake in the plant. Constitutive expression as provided by the geminiviral regulatory element may alter expression. These changes result in a change in phenotype of the transformed plant. In certain embodiments, since the expression pattern is constitutive, the expression patterns of the geminiviral regulatory elements disclosed herein are useful for many types of screening.

General categories of nucleotide sequences of interest that may be utilized with the geminiviral regulatory sequences disclosed herein include, for example, those genes involved in information, such as zinc fingers, those involved in communication, such as kinases and those involved in housekeeping, such as heat shock proteins. More specific categories of transgenes, for example, include genes encoding important traits for agronomics, insect resistance, disease resistance, herbicide resistance, environmental stress resistance (altered tolerance to cold, salt, drought, etc) and grain characteristics. Still other categories of transgenes include genes for inducing expression of exogenous products such as enzymes, cofactors, and hormones from plants and other eukaryotes as well as prokaryotic organisms. It is recognized that any gene of interest can be operably linked to the promoter of the disclosure and expressed in the plant.

By way of illustration, without intending to be limiting, the following is a list of other examples of the types of genes which may be used in connection with the regulatory sequences disclosed herein.

1. Transgenes that Confer Resistance to Insects or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones, et al., (1994) Science 266:789 (cloning of the tomato Cf-9 gene for resistance to *Cladosporium fulvum*); Martin, et al., (1993) Science 262: 1432 (tomato Pto gene for resistance to *Pseudomonas syringae* pv. tomato encodes a protein kinase); Mindrinos, et al., (1994) Cell 78:1089 (*Arabidopsis* RSP2 gene for resistance to *Pseudomonas syringae*); McDowell and Woffenden, (2003) Trends Biotechnol. 21(4):178-83 and Toyoda, et al., (2002) Transgenic Res. 11(6):567-82, herein incorporated by reference in their entirety. A plant resistant to a disease is one that is more resistant to a pathogen as compared to the wild type plant.

(B) A *Bacillus thuringiensis* protein, a derivative thereof or a synthetic polypeptide modeled thereon. See, for example, Geiser, et al., (1986) Gene 48:109, who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC Accession Numbers 40098, 67136, 31995 and 31998. Other examples of *Bacillus thuringiensis* transgenes being genetically engineered are given in the following patents and patent applications and hereby are incorporated by reference for this purpose: U.S. Pat. Nos. 5,188,960; 5,689,052; 5,880, 275; WO 91/14778; WO 99/31248; WO 01/12731; WO 99/24581; WO 97/40162 and U.S. application Ser. Nos. 10/032,717; 10/414,637 and 10/606,320, herein incorporated by reference in their entirety.

(C) An insect-specific hormone or pheromone such as an ecdysteroid and juvenile hormone, a variant thereof, a mimetic based thereon, or an antagonist or agonist thereof. See, for example, the disclosure by Hammock, et al., (1990) Nature 344:458, of baculovirus expression of cloned juvenile hormone esterase, an inactivator of juvenile hormone, herein incorporated by reference in its entirety.

(D) An insect-specific peptide which, upon expression, disrupts the physiology of the affected pest. For example, see the disclosures of Regan, (1994) J Biol. Chem. 269:9 (expression cloning yields DNA coding for insect diuretic hormone receptor); Pratt, et al., (1989) Biochem. Biophys. Res. Comm. 163:1243 (an allostatin is identified in *Diploptera puntata*); Chattopadhyay, et al., (2004) Critical Reviews in Microbiology 30(1):33-54; Zjawiony, (2004) J Nat Prod 67(2):300-310; Carlini and Grossi-de-Sa, (2002) Toxicon 40(11):1515-1539; Ussuf, et al., (2001) Curr Sci. 80(7):847-853 and Vasconcelos and Oliveira, (2004) Toxicon 44(4): 385-403, herein incorporated by reference in their entirety. See also, U.S. Pat. No. 5,266,317 to Tomalski, et al., who disclose genes encoding insect-specific toxins, herein incorporated by reference in its entirety.

(E) An enzyme responsible for a hyperaccumulation of a monterpene, a sesquiterpene, a steroid, hydroxamic acid, a phenylpropanoid derivative or another non-protein molecule with insecticidal activity.

(F) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See, PCT Application Number WO 93/02197 in the name of Scott, et al., which discloses the nucleotide sequence of a callase gene, herein incorporated by reference in its entirety. DNA molecules which contain chitinase-encoding sequences can be obtained, for example, from the ATCC under Accession Numbers 39637 and 67152. See also, Kramer, et al., (1993) Insect Biochem. Molec. Biol. 23:691, who teach the nucleotide sequence of a cDNA encoding tobacco hookworm chitinase, and Kawalleck, et al., (1993) Plant Molec. Biol. 21:673, who provide the nucleotide sequence of the parsley ubi4-2 polyubiquitin gene, U.S. patent application Ser. Nos. 10/389,432, 10/692,367 and U.S. Pat. No. 6,563,020, herein incorporated by reference in their entirety.

(G) A molecule that stimulates signal transduction. For example, see the disclosure by Botella, et al., (1994) Plant Molec. Biol. 24:757, of nucleotide sequences for mung bean calmodulin cDNA clones, and Griess, et al., (1994) Plant Physiol. 104:1467, who provide the nucleotide sequence of a maize calmodulin cDNA clone, herein incorporated by reference in their entirety.

(H) A hydrophobic moment peptide. See, PCT Application Number WO 95/16776 and U.S. Pat. No. 5,580,852 (disclosure of peptide derivatives of Tachyplesin which inhibit fungal plant pathogens) and PCT Application Number WO 95/18855 and U.S. Pat. No. 5,607,914) (teaches synthetic antimicrobial peptides that confer disease resistance), herein incorporated by reference in their entirety.

(I) A membrane permease, a channel former or a channel blocker. For example, see the disclosure by Jaynes, et al., (1993) *Plant Sci.* 89:43, of heterologous expression of a cecropin-beta lytic peptide analog to render transgenic tobacco plants resistant to *Pseudomonas solanacearum*, herein incorporated by reference in its entirety.

(J) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., (1990) *Ann. Rev. Phytopathol.* 28:451, herein incorporated by reference in its entirety. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) An insect-specific antibody or an immunotoxin derived therefrom. Thus, an antibody targeted to a critical metabolic function in the insect gut would inactivate an affected enzyme, killing the insect. Cf Taylor, et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments), herein incorporated by reference in its entirety.

(L) A virus-specific antibody. See, for example, Tavladoraki, et al., (1993) *Nature* 366:469, who show that transgenic plants expressing recombinant antibody genes are protected from virus attack, herein incorporated by reference in its entirety.

(M) A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See, Lamb, et al., (1992) *Bio/Technology* 10:1436, herein incorporated by reference in its entirety. The cloning and characterization of a gene which encodes a bean endopolygalacturonase-inhibiting protein is described by Toubart, et al., (1992) *Plant J.* 2:367, herein incorporated by reference in its entirety.

(N) A developmental-arrestive protein produced in nature by a plant. For example, Logemann, et al., (1992) *Bio/Technology* 10:305, herein incorporated by reference in its entirety, have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, (1995) *Current Biology* 5(2):128-131, Pieterse and Van Loon, (2004) *Curr. Opin. Plant Bio.* 7(4):456-64 and Somssich, (2003) *Cell* 113(7):815-6, herein incorporated by reference in their entirety.

(P) Antifungal genes (Cornelissen and Melchers, (1993) *Pl. Physiol.* 101:709-712 and Parijs, et al., (1991) *Planta* 183:258-264 and Bushnell, et al., (1998) *Can. J. of Plant Path.* 20(2):137-149. Also see, U.S. patent application Ser. No. 09/950,933, herein incorporated by reference in their entirety.

(Q) Detoxification genes, such as for fumonisin, beauvericin, moniliformin and zearalenone and their structurally related derivatives. For example, see, U.S. Pat. No. 5,792,931, herein incorporated by reference in its entirety.

(R) Cystatin and cysteine proteinase inhibitors. See, U.S. application Ser. No. 10/947,979, herein incorporated by reference in its entirety.

(S) Defensin genes. See, WO03/000863 and U.S. application Ser. No. 10/178,213, herein incorporated by reference in their entirety.

(T) Genes conferring resistance to nematodes. See, WO 03/033651 and Urwin, et. al., (1998) *Planta* 204:472-479, Williamson (1999) *Curr Opin Plant Bio.* 2(4):327-31, herein incorporated by reference in their entirety.

(U) Genes such as rcg1 conferring resistance to Anthracnose stalk rot, which is caused by the fungus *Colletotrichum graminiola*. See, Jung, et al., Generation-means analysis and quantitative trait locus mapping of Anthracnose Stalk Rot genes in Maize, *Theor. Appl. Genet.* (1994) 89:413-418, as well as, U.S. Provisional Patent Application No. 60/675,664, herein incorporated by reference in their entirety.

(V) Nucleic Acids that relate to down-regulation of expression of target genes in insect pest species by interfering ribonucleic acid (RNA) molecules, which control the insect pest species. PCT Publication WO 2007/074405 describes methods of inhibiting expression of target genes in invertebrate pests including Colorado potato beetle. PCT Publication WO 2005/110068 describes methods of inhibiting expression of target genes in invertebrate pests including in particular Western corn rootworm as a means to control insect infestation. Furthermore, PCT Publication WO 2009/091864 describes compositions and methods for the suppression of target genes from insect pest species including pests from the *Lygus* genus.

2. Transgenes that Confer Resistance to a Herbicide, for Example:

(A) A herbicide that inhibits the growing point or meristem, such as an imidazolinone or a sulfonylurea. Exemplary genes in this category code for mutant ALS and AHAS enzyme as described, for example, by Lee, et al., (1988) *EMBO J.* 7:1241 and Miki, et al., (1990) *Theor. Appl. Genet.* 80:449, respectively. See also, U.S. Pat. Nos. 5,605,011; 5,013,659; 5,141,870; 5,767,361; 5,731,180; 5,304,732; 4,761,373; 5,331,107; 5,928,937 and 5,378,824 and international publication WO 96/33270, which are incorporated herein by reference in their entirety.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes) and pyridinoxy or phenoxy proprionic acids and cycloshexones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes. See also, U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E and 5,491,288 and international publications EP1173580; WO 01/66704; EP1173581 and EP1173582, which are incorporated herein by reference in their entirety. Glyphosate resistance is also imparted to plants that express a gene that encodes a glyphosate oxido-reductase enzyme as described more fully in U.S. Pat. Nos. 5,776,760 and 5,463,175, which are incorporated herein by reference in their entirety. In addition glyphosate resistance can be imparted to plants by the over expression of genes encoding glyphosate N-acetyl-transferase. See, for example, U.S. patent application Ser. Nos. 11/405,845 and 10/427,692 and PCT Application Number US01/46227, herein incorporated by reference in their entirety. A DNA molecule encoding a mutant aroA gene can be obtained under ATCC Accession Number 39256 and the nucleotide sequence of the mutant gene is disclosed in U.S. Pat. No. 4,769,061 to Comai, herein incorporated by reference in its entirety. EP Patent Application Number 0 333 033 to Kumada, et al., and U.S. Pat. No. 4,975,374 to Goodman, et al., disclose nucleotide sequences of glutamine synthetase genes which confer resistance to herbicides such as L-phosphinothricin, herein incorporated by reference in their entirety. The nucleotide sequence of a phosphinothricin-acetyl-transferase gene is provided in EP Patent Numbers 0 242 246 and 0 242 236 to Leemans, et al., De Greef, et al., (1989) *Bio/Technology* 7:61 which describe the production of transgenic plants that express chimeric bar genes coding for phosphinothricin acetyl transferase activity, herein incorporated by reference in their entirety. See also, U.S. Pat. Nos. 5,969,213; 5,489,520; 5,550,318; 5,874,265; 5,919, 675; 5,561,236; 5,648,477; 5,646,024; 6,177,616 B1 and 5,879,903, herein incorporated by reference in their entirety. Exemplary genes conferring resistance to phenoxy proprionic acids and cycloshexones, such as sethoxydim and haloxyfop, are the Accl-S1, Accl-S2 and Accl-S3 genes described by Marshall, et al., (1992) Theor. Appl. Genet. 83:435, herein incorporated by reference in its entirety.

(C) A herbicide that inhibits photosynthesis, such as a triazine (psbA and gs+ genes) and a benzonitrile (nitrilase gene). Przibilla, et al., (1991) *Plant Cell* 3:169, herein incorporated by reference in its entirety, describe the transformation of *Chlamydomonas* with plasmids encoding mutant psbA genes. Nucleotide sequences for nitrilase genes are disclosed in U.S. Pat. No. 4,810,648 to Stalker, herein incorporated by reference in its entirety, and DNA molecules containing these genes are available under ATCC Accession Numbers 53435, 67441 and 67442. Cloning and expression of DNA coding for a glutathione S-transferase is described by Hayes, et al., (1992) *Biochem. J.* 285:173, herein incorporated by reference in its entirety.

(D) Acetohydroxy acid synthase, which has been found to make plants that express this enzyme resistant to multiple types of herbicides, has been introduced into a variety of plants (see, e.g., Hattori, et al., (1995) *Mol Gen Genet* 246:419, herein incorporated by reference in its entirety). Other genes that confer resistance to herbicides include: a gene encoding a chimeric protein of rat cytochrome P4507A1 and yeast NADPH-cytochrome P450 oxidoreductase (Shiota, et al., (1994) *Plant Physiol.* 106(1):17-23), genes for glutathione reductase and superoxide dismutase (Aono, et al., (1995) *Plant Cell Physiol* 36:1687, and genes for various phosphotransferases (Datta, et al., (1992) *Plant Mol Biol* 20:619), herein incorporated by reference in their entirety.

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 B1; 6,282,837 B1 and 5,767,373; and international publication number WO 01/12825, herein incorporated by reference in their entirety.

3. Transgenes that Confer or Contribute to an Altered Grain Characteristic, Such as:
  (A) Altered fatty acids, for example, by
    (1) Down-regulation of stearoyl-ACP desaturase to increase stearic acid content of the plant. See, Knultzon, et al., (1992) *Proc. Natl. Acad. Sci. USA* 89:2624 and WO99/64579 (Genes for Desaturases to Alter Lipid Profiles in Corn), herein incorporated by reference in their entirety,
    (2) Elevating oleic acid via FAD-2 gene modification and/or decreasing linolenic acid via FAD-3 gene modification (see, U.S. Pat. Nos. 6,063,947; 6,323,392; 6,372,965 and WO 93/11245, herein incorporated by reference in their entirety),
    (3) Altering conjugated linolenic or linoleic acid content, such as in WO 01/12800, herein incorporated by reference in its entirety,
    (4) Altering LEC1, AGP, Dek1, Superal1, milps, various lpa genes such as lpa1, lpa3, hpt or hggt. For example, see, WO 02/42424, WO 98/22604, WO 03/011015, 6,825,397, US Patent Application Publication Numbers 2003/0079247, 2003/0204870, WO02/057439, WO03/011015 and Rivera-Madrid, et. al., (1995) *Proc. Natl. Acad. Sci.* 92:5620-5624, herein incorporated by reference in their entirety.
  (B) Altered phosphorus content, for example, by the
    (1) Introduction of a phytase-encoding gene would enhance breakdown of phytate, adding more free phosphate to the transformed plant. For example, see, Van Hartingsveldt, et al., (1993) *Gene* 127:87, for a disclosure of the nucleotide sequence of an *Aspergillus niger* phytase gene, herein incorporated by reference in its entirety.
    (2) Up-regulation of a gene that reduces phytate content. In maize, this, for example, could be accomplished, by cloning and then re-introducing DNA associated with one or more of the alleles, such as the LPA alleles, identified in maize mutants characterized by low levels of phytic acid, such as in Raboy, et al., (1990) *Maydica* 35:383 and/or by altering inositol kinase activity as in WO 02/059324, US Patent Application Publication Number 2003/0009011, WO 03/027243, US Patent Application Publication Number 2003/0079247, WO 99/05298, U.S. Pat. Nos. 6,197,561, 6,291,224, 6,391, 348, WO2002/059324, US Patent Application Publication Number 2003/0079247, WO98/45448, WO99/55882, WO01/04147, herein incorporated by reference in their entirety.
  (C) Altered carbohydrates effected, for example, by altering a gene for an enzyme that affects the branching pattern of starch or a gene altering thioredoxin such as NTR and/or TRX (see, U.S. Pat. No. 6,531,648, which is incorporated by reference in its entirety) and/or a gamma zein knock out or mutant such as cs27 or TUSC27 or en27 (see, U.S. Pat. No. 6,858,778 and US Patent Application Publication Numbers 2005/0160488 and 2005/0204418; which are incorporated by reference in its entirety). See, Shiroza, et al., (1988) *J. Bacterial.* 170:810 (nucleotide sequence of *Streptococcus mutans* fructosyltransferase gene), Steinmetz, et al., (1985) *Mol. Gen. Genet.* 200:220 (nucleotide sequence of *Bacillus subtilis* levansucrase gene), Pen, et al., (1992) *Bio/Technology* 10:292 (production of transgenic plants that express *Bacillus licheniformis* alpha-amylase), Elliot, et al., (1993) *Plant Molec. Biol.* 21:515 (nucleotide sequences of tomato invertase genes), Søgaard, et al., (1993) *J. Biol. Chem.* 268:22480 (site-directed mutagenesis of barley alpha-amylase gene) and Fisher, et al., (1993) *Plant Physiol.* 102:1045 (maize endosperm starch branching enzyme II), WO 99/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)), herein incorporated by reference in their entirety. The fatty acid modification genes mentioned above may also be used to affect starch content and/or composition through the interrelationship of the starch and oil pathways.

(D) Altered antioxidant content or composition, such as alteration of tocopherol or tocotrienols. For example, see U.S. Pat. No. 6,787,683, US Patent Application Publication Number 2004/0034886 and WO 00/68393 involving the manipulation of antioxidant levels through alteration of a phytl prenyl transferase (ppt), WO 03/082899 through alteration of a homogentisate geranyl geranyl transferase (hggt), herein incorporated by reference in their entirety.

(E) Altered essential seed amino acids. For example, see U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO99/40209 (alteration of amino acid compositions in seeds), WO99/29882 (methods for altering amino acid content of proteins), U.S. Pat. No. 5,850,016 (alteration of amino acid compositions in seeds), WO98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO98/56935 (plant amino acid biosynthetic enzymes), WO98/45458 (engineered seed protein having higher percentage of essential amino acids), WO98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO96/01905 (increased threonine), WO95/15392 (increased lysine), US Patent Application Publication Number 2003/0163838, US Patent Application Publication Number 2003/0150014, US Patent Application Publication Number 2004/0068767, U.S. Pat. No. 6,803,498, WO01/79516, and WO00/09706 (Ces A: cellulose synthase), U.S. Pat. No. 6,194,638 (hemicellulose), U.S. Pat. No. 6,399,859 and US Patent Application Publication Number 2004/0025203 (UDPGdH), U.S. Pat. No. 6,194,638 (RGP), herein incorporated by reference in their entirety.

4. Genes that Control Male-Sterility

There are several methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511, herein incorporated by reference in their entirety. In addition to these methods, Albertsen, et al., U.S. Pat. No. 5,432,068, herein incorporated by reference in its entirety, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant and thus creating a plant that is male sterile because the inducible promoter is not "on" resulting in the male fertility gene not being transcribed. Fertility is restored by inducing, or turning "on", the promoter, which in turn allows the gene conferring male fertility to be transcribed.

(A) Introduction of a deacetylase gene under the control of a tapetum-specific promoter and with the application of the chemical N—Ac-PPT (WO 01/29237, herein incorporated by reference in its entirety).

(B) Introduction of various stamen-specific promoters (WO 92/13956, WO 92/13957, herein incorporated by reference in their entirety).

(C) Introduction of the barnase and the barstar gene (Paul, et al., (1992) *Plant Mol. Biol.* 19:611-622, herein incorporated by reference in its entirety).

For additional examples of nuclear male and female sterility systems and genes, see also, U.S. Pat. Nos. 5,859,341; 6,297,426; 5,478,369; 5,824,524; 5,850,014 and 6,265,640; all of which are hereby incorporated by reference in their entirety.

5. Genes that Create a Site for Site Specific DNA Integration

This includes the introduction of FRT sites that may be used in the FLP/FRT system and/or Lox sites that may be used in the Cre/Loxp system. For example, see Lyznik, et al., (2003) *Plant Cell Rep* 21:925-932 and WO 99/25821, which are hereby incorporated by reference in their entirety. Other systems that may be used include the Gin recombinase of phage Mu (Maeser, et al., 1991; Vicki Chandler, *The Maize Handbook* ch. 118 (Springer-Verlag 1994), the Pin recombinase of *E. coli* (Enomoto, et al., 1983), and the R/RS system of the pSR1 plasmid (Araki, et al., 1992), herein incorporated by reference in their entirety.

6. Genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress. For example, see WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, WO2000060089, WO2001026459, WO2001035725, WO2001034726, WO2001035727, WO2001036444, WO2001036597, WO2001036598, WO2002015675, WO2002017430, WO2002077185, WO2002079403, WO2003013227, WO2003013228, WO2003014327, WO2004031349, WO2004076638, WO9809521, and WO9938977 describing genes, including CBF genes and transcription factors effective in mitigating the negative effects of freezing, high salinity, and drought on plants, as well as conferring other positive effects on plant phenotype; US Patent Application Publication Number 2004/0148654 and WO01/36596 where abscisic acid is altered in plants resulting in improved plant phenotype such as increased yield and/or increased tolerance to abiotic stress; WO2000/006341, WO04/090143, U.S. patent application Ser. No. 10/817,483 and U.S. Pat. No. 6,992,237, where cytokinin expression is modified resulting in plants with increased stress tolerance, such as drought tolerance, and/or increased yield, herein incorporated by reference in their entirety. Also see WO0202776, WO2003052063, JP2002281975, U.S. Pat. No. 6,084,153, WO0164898, U.S. Pat. Nos. 6,177,275 and 6,107,547 (enhancement of nitrogen utilization and altered nitrogen responsiveness), herein incorporated by reference in their entirety. For ethylene alteration, see US Patent Application Publication Number 2004/0128719, US Patent Application Publication Number 2003/0166197 and WO200032761, herein incorporated by reference in their entirety. For plant transcription factors or transcriptional regulators of abiotic stress, see, e.g., US Patent Application Publication Number 2004/0098764 or US Patent Application Publication Number 2004/0078852, herein incorporated by reference in their entirety.

Other genes and transcription factors that affect plant growth and agronomic traits such as yield, flowering, plant growth and/or plant structure, can be introduced or introgressed into plants, see, e.g., WO97/49811 (LHY), WO98/56918 (ESD4), WO97/10339 and U.S. Pat. No. 6,573,430 (TFL), U.S. Pat. No. 6,713,663 (FT), WO96/14414 (CON), WO96/38560, WO01/21822 (VRN1), WO00/44918 (VRN2), WO99/49064 (GI), WO00/46358 (FRI), WO97/29123, U.S. Pat. Nos. 6,794,560, 6,307,126 (GAI), WO99/09174 (D8 and Rht) and WO2004076638 and WO2004031349 (transcription factors), herein incorporated by reference in their entirety.

"RNAi" refers to a series of related techniques to reduce the expression of genes (see, for example, U.S. Pat. No. 6,506,559). Some techniques referred to by other names are now thought to rely on the same mechanism, but are given different names in the literature. These include "antisense inhibition," the production of antisense RNA transcripts capable of suppressing the expression of the target protein, and "co-suppression" or "sense-suppression," which refer to the production of sense RNA transcripts capable of suppressing the expression of identical or substantially similar foreign or endogenous genes (U.S. Pat. No. 5,231,020, incorporated herein by reference in its entirety). Such techniques rely on the use of constructs resulting in the accumulation of double stranded RNA with one strand complementary to the target gene to be silenced. The geminiviral regulatory sequences disclosed herein may be used to drive expression of constructs that will result in RNA interference including microRNAs and siRNAs.

The isolated regulatory element sequences disclosed herein can be modified to provide for a range of expression levels of the heterologous nucleotide sequence. Thus, less than the entire regulatory element region may be utilized and the ability to drive expression of the nucleotide sequence of interest retained. It is recognized that expression levels of the mRNA may be altered in different ways with deletions of portions of the promoter sequences. The mRNA expression levels may be decreased, or alternatively, expression may be increased as a result of promoter deletions if, for example, there is a negative regulatory element (for a repressor) that is removed during the truncation process. Generally, at least about 20 nucleotides of an isolated promoter sequence will be used to drive expression of a nucleotide sequence.

Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903; and Joshi, et al., (1987) *Nucleic Acid Res.* 15:9627-9639.

Expression cassettes comprising sequences disclosed herein may also contain at least one additional nucleotide sequence for a gene to be cotransformed into the organism. Alternatively, the additional sequence(s) can be provided on another expression cassette.

Where appropriate, the nucleotide sequences whose expression is to be under the control of the early-endosperm-tissue-preferred promoter sequence of the present disclosure and any additional nucleotide sequence(s) may be optimized for increased expression in the transformed plant. That is, these nucleotide sequences can be synthesized using plant preferred codons for improved expression. See, for example, Campbell and Gowri, (1990) *Plant Physiol.* 92:1-11, for a discussion of host-preferred codon usage. Methods are available in the art for synthesizing plant-preferred genes. See, for example, U.S. Pat. Nos. 5,380,831, 5,436,391 and Murray, et al., (1989) *Nucleic Acids Res.* 17:477-498.

Additional sequence modifications are known to enhance gene expression in a cellular host. These include elimination of sequences encoding spurious polyadenylation signals, exon-intron splice site signals, transposon-like repeats and other such well-characterized sequences that may be deleterious to gene expression. The G-C content of the heterologous nucleotide sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences may act to enhance translation. Translation leaders are known in the art and include, without limitation: picornavirus leaders, for example, EMCV leader (Encephalomyocarditis 5' noncoding region) (Elroy-Stein, et al., (1989) *Proc. Nat. Acad. Sci. USA* 86:6126-6130); potyvirus leaders, for example, TEV leader (Tobacco Etch Virus) (Allison, et al., (1986) *Virology* 154:9-20); MDMV leader (Maize Dwarf Mosaic Virus); human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) *Molecular Biology of RNA*, pages 237-256) and maize chlorotic mottle virus leader (MCMV) (Lommel, et al., (1991) *Virology* 81:382-385), herein incorporated by reference in their entirety. See, also, Della-Cioppa, et al., (1987) *Plant Physiology* 84:965-968, herein incorporated by reference in its entirety. Methods known to enhance mRNA stability may also be utilized, for example, introns, such as the maize Ubiquitin intron (Christensen and Quail, (1996) *Transgenic Res.* 5:213-218; Christensen, et al., (1992) *Plant Molecular Biology* 18:675-689) or the maize Adh1 intron (Kyozuka, et al., (1991)*Mol. Gen. Genet.* 228:40-48; Kyozuka, et al., (1990) *Maydica* 35:353-357) and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, for example, transitions and transversions, may be involved.

Reporter genes or selectable marker genes may also be included in expression cassettes. Examples of suitable reporter genes known in the art can be found in, for example, Jefferson, et al., (1991) in Plant Molecular Biology Manual, ed. Gelvin, et al., (Kluwer Academic Publishers), pp. 1-33;

DeWet, et al., (1987) *Mol. Cell. Biol.* 7:725-737; Goff, et al., (1990) *EMBO J.* 9:2517-2522; Kain, et al., (1995) *Bio Techniques* 19:650-655 and Chiu, et al., (1996) *Current Biology* 6:325-330.

Selectable marker genes for selection of transformed cells or tissues may include genes that confer antibiotic resistance or resistance to herbicides. Examples of suitable selectable marker genes include, but are not limited to, genes encoding resistance to chloramphenicol (Herrera Estrella, et al., (1983) *EMBO J.* 2:987-992); methotrexate (Herrera Estrella, et al., (1983) *Nature* 303:209-213; Meijer, et al., (1991) *Plant Mol. Biol.* 16:807-820); hygromycin (Waldron, et al., (1985) *Plant Mol. Biol.* 5:103-108 and Zhijian, et al., (1995) *Plant Science* 108:219-227); streptomycin (Jones, et al., (1987) *Mol. Gen. Genet.* 210:86-91); spectinomycin (Bretagne-Sagnard, et al., (1996) *Transgenic Res.* 5:131-137); bleomycin (Hille, et al., (1990) *Plant Mol. Biol.* 7:171-176); sulfonamide (Guerineau, et al., (1990) *Plant Mol. Biol.* 15:127-36); bromoxynil (Stalker, et al., (1988) *Science* 242:419-423); glyphosate (Shaw, et al., (1986) *Science* 233:478-481 and U.S. patent application Ser. Nos. 10/004,357 and 10/427,692); phosphinothricin (DeBlock, et al., (1987) *EMBO J.* 6:2513-2518), herein incorporated by reference in their entirety.

Other genes that could serve utility in the recovery of transgenic events would include, but are not limited to, examples such as GUS (beta-glucuronidase; Jefferson, (1987) *Plant Mol. Biol. Rep.* 5:387), GFP (green fluorescence protein; Chalfie, et al., (1994) *Science* 263:802), luciferase (Riggs, et al., (1987) *Nucleic Acids Res.* 15(19): 8115 and Luehrsen, et al., (1992) *Methods Enzymol.* 216: 397-414) and the maize genes encoding for anthocyanin production (Ludwig, et al., (1990) *Science* 247:449).

Expression cassette comprising the sequences of SEQ ID NOs: 1-13 operably linked to a nucleotide sequence of interest may be used to transform any plant. In this manner, genetically modified plants, plant cells, plant tissue, seed, root and the like may be obtained.

Certain disclosed methods involve introducing a polynucleotide into a plant. As used herein, "introducing" is intended to mean presenting to the plant the polynucleotide in such a manner that the sequence gains access to the interior of a cell of the plant. The methods of the disclosure do not depend on a particular method for introducing a sequence into a plant, only that the polynucleotide gains access to the interior of at least one cell of the plant. Methods for introducing polynucleotide into plants are known in the art including, but not limited to, stable transformation methods, transient transformation methods and virus-mediated methods.

A "stable transformation" is a transformation in which the polynucleotide construct introduced into a plant integrates into the genome of the plant and is capable of being inherited by the progeny thereof. "Transient transformation" means that a polynucleotide is introduced into the plant and does not integrate into the genome of the plant.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway, et al., (1986) *Biotechniques* 4:320-334), electroporation (Riggs, et al., (1986) *Proc. Natl. Acad. Sci. USA* 83:5602-5606), *Agrobacterium*-mediated transformation (Townsend, et al., U.S. Pat. No. 5,563,055 and Zhao, et al., U.S. Pat. No. 5,981,840), direct gene transfer (Paszkowski, et al., (1984) *EMBO J.* 3:2717-2722) and ballistic particle acceleration (see, for example, U.S. Pat. Nos. 4,945,050; 5,879,918; 5,886,244; 5,932,782; Tomes, et al., (1995) in Plant Cell, Tissue, and Organ Culture: Fundamental Methods, ed. Gamborg and Phillips (Springer-Verlag, Berlin); McCabe, et al., (1988) *Biotechnology* 6:923-926) and Lec1 transformation (WO 00/28058). Also see, Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P:175-182 (soybean); Singh, et al., (1998) *Theon. Appl. Genet.* 96:319-324 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature* (London) 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in The Experimental Manipulation of Ovule Tissues, ed. Chapman, et al., (Longman, New York), pp. 197-209 (pollen); Kaeppler, et al., (1990) *Plant Cell Reports* 9:415-418 and Kaeppler, et al., (1992) *Theon. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., and (1996) *Nature Biotechnology* 14:745-750 (maize via *Agrobacterium tumefaciens*).

In one embodiment, DNA constructs comprising the disclosed sequences SEQ ID NOs: 1-13 can be provided to a plant using a variety of transient transformation methods. Such transient transformation methods include, but are not limited to, viral vector systems and the precipitation of the polynucleotide in a manner that precludes subsequent release of the DNA. Thus, transcription from the particle-bound DNA can occur, but the frequency with which it is released to become integrated into the genome is greatly reduced. Such methods include the use of particles coated with polyethylimine (PEI; Sigma #P3143).

In other embodiments, a polynucleotide may be introduced into plants by contacting plants with a virus or viral nucleic acids. Generally, such methods involve incorporating a polynucleotide construct of the disclosure within a viral DNA or RNA molecule. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931 and Porta, et al., (1996) *Molecular Biotechnology* 5:209-221.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855 and WO99/25853, all of which are herein incorporated by reference in their entirety. Briefly, the polynucleotide of the disclosure can be contained in transfer cassette flanked by two non-identical recombination sites. The transfer cassette is introduced into a plant having stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick, et al., (1986) *Plant Cell Reports* 5:81-84. These plants may then be grown, and either pollinated with the same transformed strain or different strains, and the resulting progeny having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present disclosure provides transformed seed (also referred to as "transgenic seed") having a nucleotide construct, for example, an expression cassette comprising one of SEQ ID NOs: 1-13, stably incorporated into its genome.

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, (1988) In: Methods for Plant Molecular Biology, (Eds.), Academic Press, Inc., San Diego, Calif.). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the embodiments containing a desired polynucleotide is cultivated using methods well known to one skilled in the art.

The embodiments provide compositions for screening compounds that modulate expression within plants. The vectors, cells and plants can be used for screening candidate molecules for agonists and antagonists of the geminiviral regulatory element sequences of SEQ ID NOs: 1-13. For example, a reporter gene can be operably linked to a geminiviral regulatory element sequence and expressed as a transgene in a plant. Compounds to be tested are added and reporter gene expression is measured to determine the effect on promoter activity.

In one embodiment, the geminiviral regulatory element sequences SEQ ID NOs: 1-13 may be edited or inserted into a plant by genome editing using a CRISPR/Cas9 system.

CRISPR loci (Clustered Regularly Interspaced Short Palindromic Repeats) (also known as SPIDRs—SPacer Interspersed Direct Repeats) constitute a family of recently described DNA loci. CRISPR loci consist of short and highly conserved DNA repeats (typically 24 to 40 bp, repeated from 1 to 140 times—also referred to as CRISPR-repeats) which are partially palindromic. The repeated sequences (usually specific to a species) are interspaced by variable sequences of constant length (typically 20 to 58 by depending on the CRISPR locus (WO2007/025097 published Mar. 1, 2007).

Cas gene relates to a gene that is generally coupled, associated or close to or in the vicinity of flanking CRISPR loci. The terms "Cas gene", "CRISPR-associated (Cas) gene" are used interchangeably herein. (Haft et al. (2005) Computational Biology, PLoS Comput Biol 1(6): e60. doi: 10.1371/journal.pcbi.0010060). As described therein, 41 CRISPR-associated (Cas) gene families are described, in addition to the four previously known gene families. It shows that CRISPR systems belong to different classes, with different repeat patterns, sets of genes, and species ranges. The number of Cas genes at a given CRISPR locus can vary between species.

Cas endonuclease relates to a Cas protein encoded by a Cas gene, wherein said Cas protein is capable of introducing a double strand break into a DNA target sequence. The Cas endonuclease is guided by a guide polynucleotide to recognize and optionally introduce a double strand break at a specific target site into the genome of a cell (U.S. 2015/0082478). The guide polynucleotide/Cas endonuclease system includes a complex of a Cas endonuclease and a guide polynucleotide that is capable of introducing a double strand break into a DNA target sequence. The Cas endonuclease unwinds the DNA duplex in close proximity of the genomic target site and cleaves both DNA strands upon recognition of a target sequence by a guide RNA if a correct protospacer-adjacent motif (PAM) is approximately oriented at the 3' end of the target sequence. The Cas endonuclease can be introduced directly into a cell by any method known in the art, for example, but not limited to transient introduction methods, transfection and/or topical application.

As used herein, the term "guide RNA" relates to a synthetic fusion of two RNA molecules, a crRNA (CRISPR RNA) comprising a variable targeting domain, and a tracrRNA. In one embodiment, the guide RNA comprises a variable targeting domain of 12 to 30 nucleotide sequences and a RNA fragment that can interact with a Cas endonuclease.

As used herein, the term "guide polynucleotide", relates to a polynucleotide sequence that can form a complex with a Cas endonuclease and enables the Cas endonuclease to recognize and optionally cleave a DNA target site (U.S. 2015/0082478). The guide polynucleotide can be a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide RNA".

The term "variable targeting domain" or "VT domain" is used interchangeably herein and includes a nucleotide sequence that is complementary to one strand (nucleotide sequence) of a double strand DNA target site. The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides.

The variable targeting domain can be composed of a DNA sequence, a RNA sequence, a modified DNA sequence, a modified RNA sequence, or any combination thereof.

The term "Cas endonuclease recognition domain" or "CER domain" of a guide polynucleotide is used interchangeably herein and includes a nucleotide sequence (such as a second nucleotide sequence domain of a guide polynucleotide), that interacts with a Cas endonuclease polypeptide. The CER domain can be composed of a DNA sequence, a RNA sequence, a modified DNA sequence, a modified RNA sequence (see for example modifications described herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a tetraloop sequence, such as, but not limiting to a GAAA tetraloop seqence.

All publications, patents and patent applications mentioned in the specification are indicative of the level of those skilled in the art to which this disclosure pertains. All publications, patents and patent applications are herein incorporated by reference to the same extent as if each individual publication, patent or patent application was specifically and individually indicated to be incorporated by reference.

The above description of various illustrated embodiments of the disclosure is not intended to be exhaustive or to limit the scope to the precise form disclosed. While specific embodiments of examples are described herein for illustrative purposes, various equivalent modifications are possible within the scope of the disclosure, as those skilled in the relevant art will recognize. The teachings provided herein can be applied to other purposed, other than the examples described above. Numerous modifications and variations are possible in light of the above teachings and, therefore, are within the scope of the appended claims.

These and other changes may be made in light of the above detailed description. In general, in the following claims, the terms used should not be construed to limit the scope to the specific embodiments disclosed in the specification and the claims.

Efforts have been made to ensure accuracy with respect to the numbers used (e.g. amounts, temperature, concentrations, etc.), but some experimental errors and deviations should be allowed for. Unless otherwise indicated, parts are parts by weight; molecular weight is average molecular weight; temperature is in degrees centigrade; and pressure is at or near atmospheric.

EXPERIMENTAL

Example 1: Geminiviral Regulatory Element Sequences

The geminiviral regulatory element sequences (SEQ ID NO: 1-13) were obtained through a search of GenBank Genomes for viral genomes that had been sequenced and belonged to the Geminiviridae family. Analysis of the Bean Yellow Dwarf Virus (BYDV), Beet Mild Curly Top Virus (BMTV), East African Cassava Mosaic (Cameroon) Virus (EACMCV), Hollyhock Leaf Crumple Virus (HLCV), Horseradish Curly Top Virus (HCTV), Macroptilium Yellow Mosaic Florida Virus (MYMFV), Sugarcane Streak (Egypt) Virus (SSEV), Sugarcane Streak Virus (SSV), Tomato.

Curly Stunt Virus (South Africa) (TCSVSA), and Wheat Dwarf Virus (WDWV) genomes revealed intergenic regions which were targeted for functional analysis of regulatory elements that would control gene expression in plant cells. One sequence from each was selected to be synthesized and tested in plants. The sequences are set forth in SEQ ID NOs: 1-13. The entire sequence is referred to as the full-length (FL) regulatory element (BYDV FL, BMTV FL, EACMCV FL, HLCV FL, HCTV FL, MYMFV FL, SSEV FL, SSV FL, TCSVSA FL, and WDWV FL).

Example 2: Expression Analysis of the BYDV FL Regulatory Element

The geminiviral regulatory elements were operably linked to an ADH1 intron1 (ADH1 intron1) and the 0-glucuronidase (GUS) gene to understand the expression pattern directed by each geminiviral regulatory element in plants. ADH1 intron1 was included for the purpose of increased expression as it has been shown in cereal plant cells that the expression of transgenes is enhanced by the presence of some 5' proximal introns (See Callis et al. (1987) *Genes and Development* 1: 1183-1200; Kyozuka et al. (1990) *Maydica* 35:353-357). Ten events were regenerated for analysis of each regulatory element by histochemically staining tissues for GUS activity. Leaf and root material was assayed at V5-V6 stages and stalk, tassel and pollen were assayed at R1-R2 stages. V or vegetative growth stages in maize development are determined by the number of collared leaves on the plant. Therefore, a plant at V5 stage has 5 fully collared leaves. R or reproductive stages are determined once the plant flowers. R1 stage is noted by the emergence of silks outside the husk and R2 is when the silks start to dry out.

Geminiviral regulatory element directed expression in maize plants is highlighted in Table 2. All the elements directed expression in more than one tissue; however, expression levels were generally less than the Ubi-1 control. The Ubi-1 promoter and intron from *Zea mays* was operably linked to the GUS gene for comparison in the analysis. This well characterized regulatory combination drives strong expression in most tissues of maize. In these studies, expression was strong in all tissues and across the developmental stages described for the geminiviral regulatory elements.

TABLE 2

Geminiviral Promoter Expression Pattern in Maize Plants

|  | V5-V6 | | R1-R2 | | | SEQ ID NO: |
|---|---|---|---|---|---|---|
|  | Leaf | Root | Stalk | Tassel | Pollen |  |
| BYDV FL: ADH1 intron1 | +++ | ++ | ++ | +++ | − | 4 |
| TCSVSA FL: ADH1 intron1 | ++ | + | + | ++ | − | 12 |
| HLCV FL: ADH1 intron1 | + | + | ++ | + | − | 7 |
| BMTV FL: ADH1 intron1 | ++ | + | + | + | + | 5 |
| EACMCV FL: ADH1 Intron1 | + | + | + | + | − | 6 |
| HCTV FL: ADH1 Intron1 | + | + | + | ++ | ++ | 8 |
| MYMFV FL: ADH1 intron1 | − | + | + | + | + | 9 |
| SSEV FL: ADH1 intron1 | + | + | + | ++ | + | 10 |
| SSV FL: ADH1 intron1 | + | + | + | ++ | + | 11 |
| WDWV FL: ADH1 intron1 | ++ | + | + | ++ | + | 13 |
| Ubi-1: Ubi-1 intron | +++ | +++ | +++ | +++ | +++ |  |

+ = expression observed in histochemically stained tissue
− = low or no expression detected A second set of expression vectors was constructed using a subset of geminiviral regulatory elements with each element operably linked to 3 copies of the transcriptional enhancer from the Cauliflower Mosaic Virus 35S promoter, the first intron of the maize alcohol dehydrogenase gene 1 (ADH1 intron1) and an insecticidal gene (IG1). This subset of elements included BYDV FL, HLCV FL, MYMFV FL, SSV FL, TCSVSA FL, and WDWV FL. In a third expression vector, the same subset of geminiviral regulatory elements were operably linked to 2 or 3 copies of the transcriptional enhancer from the Mirabilis Mosaic Virus (MMV) promoter, the first intron of the maize alcohol dehydrogenase gene 1 (ADH1 intron1) and the IG1 insecticidal gene. The purpose of the enhancers was to increase expression directed by the geminiviral regulatory elements and determine if one enhancer performed better than the other. The Ubi-1 promoter and intron from *Zea mays* operably linked to the IG1 gene was used for comparison.

Stable transformed maize plants in excess of 10 events per vector were created using *Agrobacterium* protocols (detailed in Example 3) to allow for the characterization of expression by each geminiviral regulatory element construct. Plants were grown to V5-V6 stages under greenhouse conditions and sampled for leaf material to use in enzyme-linked immunosorbent assays (ELISA) and plant efficacy assays with insects (Tables 3 and 4). Feeding leaf material to insects provides a rapid assessment of expression, as sufficient protein levels are needed to protect the sample from the insects. Insufficient expression will result in feeding and decimation of the sample.

The plants were allowed to grow to R1-R2 stages when stalk and pollen expression was determined (Table 3). Insect feeding was evaluated on developing ears and kernel expression was determined once the plant and ears reached maturity.

Results indicated that the addition of an enhancer elevated the performance of the geminiviral regulatory elements to levels that were more similar to Ubi-1 and its intron in both gene expression and plant efficacy (Tables 3 and 4). The only exceptions were pollen and kernels where expression levels remained low. The 2×MMV enhancer generally performed better than the (3×)35S enhancer.

TABLE 3

Geminiviral Regulatory Element Directed IG1 Expression in Maize Plants.

|  | 2XMMV (SEQ ID NO: 2) | | | | 3X35S | | | | SEQ ID NO: |
|---|---|---|---|---|---|---|---|---|---|
|  | V5-V6 | R1-R2 | | Maturity | V5-V6 | R1-R2 | | Maturity |  |
|  | Leaf | Stalk | Pollen | Kernel | Leaf | Stalk | Pollen | Kernel |  |
| BYDV FL: ADH1 intron1 | 82% | 40% | 3% | 0% | 55% | 92% | 0% | 2% | 4 |
| TCSVSA FL: ADH1 intron1 | 136% | 172% | 4% | 37% | 14% | 0% | 0% | n.d. | 12 |
| HLCV FL: ADH1 intron1 | 74% | 140% | 2% | 4% | 65% | 85% | 0% | 2% | 7 |
| MYMFV FL: ADH1 intron1 | 106% | 185% | 7% | 18% | 49% | 132% | 2% | 5% | 9 |
| SSV FL: ADH1 intron1 | 32% | 39% | 20% | 0% | n.d. | 120% | 17% | 0% | 11 |
| WDWV FL: ADH1 intron1 | 102% | 71% | 16% | 22% | 78% | 47% | 5% | 8% | 13 |
| Ubi-1: Ubi-1 intron | 100% | 100% | 100% | 100% | 100% | 100% | 100% | 100% |  |
| untransformed (negative control) | 0% | 0% | 0% | n.d. | 0% | 0% | 0% | n.d. |  |

Expression data is represented as a percentage of Ubi-1 expression: n.d. indicates no data is available.

TABLE 4

Enhancer/Promoter Expression and Efficacy Comparison in Maize

| | V5-V6 | | R1-R2 | | | |
|---|---|---|---|---|---|---|
| | Leaf | Leaf Efficacy | Stalk | Pollen | Kernels | Ear Efficacy |
| BYDV FL: ADH1 intron1 | 1 | 2 | 0 | 0 | 0 | 0 |
| (3x)35S enhancer: BYDV FL: ADH1 intron1 | 3 | 3 | 4 | 0 | 0 | 3 |
| 2xMMV enhancer: BYDV FL: ADH1 intron1 | 4 | 4 | 3 | 0 | 0 | 4 |
| HLCV FL: ADH1 intron1 | 0 | 0 | 0 | 0 | 0 | 1 |
| (3x)35S enhancer: HLCV FL: ADH1 intron1 | 3 | 4 | 3 | 0 | 3 | 1 |
| 2xMMV enhancer: HLCV FL: ADH1 intron1 | 5 | 4 | 4 | 0 | 4 | 1 |
| 3xMMV enhancer: HLCV FL: ADH1 intron1 | 4 | 4 | 3 | nd | 4 | 2 |
| TCSVSA FL: ADH1 intron1 | 0 | nd | 0 | 1 | nd | 0 |
| 2xMMV enhancer: TCSVSA FL: ADH1 intron1 | 5 | 4 | 5 | 0 | nd | 5 |
| 3xMMV enhancer: TCSVSA FL: ADH1 intron1 | 5 | 4 | 5 | 0 | nd | 5 |
| Ubi-1 | 4 | 4 | 4 | 4 | 4 | 4 |
| untransformed (negative control) | 0 | 0 | 0 | 0 | 0 | 0 |

Data represented by a 0-5 scale with 0 indicating very low expression or efficacy and 5 indicating high expression or plant efficacy against feeding insects.

Example 3: *Agrobacterium*-Mediated Transformation of Maize and Regeneration of Transgenic Plants For *Agrobacterium*-mediated transformation of maize with a regulatory element sequence of the disclosure, the method of Zhao was employed (U.S. Pat. No. 5,981,840, and PCT patent publication WO98/32326). Briefly, immature embryos were isolated from maize and the embryos contacted with a suspension of *Agrobacterium* under conditions whereby the bacteria were capable of transferring the regulatory element sequence of the disclosure to at least one cell of at least one of the immature embryos (step 1: the infection step). In this step the immature embryos were immersed in an *Agrobacterium* suspension for the initiation of inoculation. The embryos were co-cultured for a time with the *Agrobacterium* (step 2: the co-cultivation step). The immature embryos were cultured on solid medium following the infection step. Following the co-cultivation period an optional "resting" step was performed. In this resting step, the embryos were incubated in the presence of at least one antibiotic known to inhibit the growth of *Agrobacterium* without the addition of a selective agent for plant transformants (step 3: resting step). Next, inoculated embryos were cultured on medium containing a selective agent and growing transformed calli were recovered (step 4: the selection step). Plantlets were regenerated from the calli (step 5: the regeneration step) prior to transfer to the greenhouse.

What is claimed is:

1. A recombinant polynucleotide comprising a heterologous transcribable polynucleotide molecule operably linked to a regulatory element polynucleotide, wherein the regulatory element polynucleotide is selected from the group consisting of:
   (a) a polynucleotide having at least 95 percent sequence identity to the sequence of SEQ ID NO: 12 and having regulatory activity;
   (b) a polynucleotide comprising the nucleic acid sequence set forth in SEQ ID NO: 12; and
   (c)
   (d) a functional fragment comprising at least 100 contiguous nucleotides of SEQ ID NO: 12, wherein the nucleic acid sequence has regulatory activity.

2. The recombinant polynucleotide of claim 1, wherein the recombinant polynucleotide further comprises a polynucleotide sequence of SEQ ID NO: 1, 2, or 3.

3. A DNA construct comprising a heterologous transcribable polynucleotide molecule operably linked to a regulatory element polynucleotide, wherein the regulatory element polynucleotide comprises a polynucleotide sequence selected from the group consisting of:
   (a) a polynucleotide having at least 95 percent sequence identity to the nucleic acid sequence of SEQ ID NO: 12, having regulatory activity;
   (b) a polynucleotide comprising the nucleic acid sequence set forth in SEQ ID NO: 12; and
   (c)
   (d) a functional fragment of at least 100 contiguous nucleotides of SEQ ID NO: 12 having regulatory activity.

4. The DNA construct of claim 3, further comprising a polynucleotide sequence of SEQ ID NO: 1, 2, or 3.

5. The DNA construct of claim 3, wherein the heterologous transcribable polynucleotide molecule is a gene of agronomic interest.

6. The DNA construct of claim 5, wherein the heterologous transcribable polynucleotide molecule is a gene capable of providing herbicide resistance in plants.

7. The DNA construct of claim 5, wherein the heterologous transcribable polynucleotide molecule is a gene capable of providing plant pest control in plants.

8. A heterologous cell stably transformed with the DNA construct of claim 3.

9. A transgenic plant or plant cell stably transformed with the DNA construct of claim 3.

10. The transgenic plant or plant cell of claim 9, wherein the transgenic plant or plant cell is a dicotyledon plant or plant cell.

11. The transgenic plant or plant cell of claim 9, wherein the transgenic plant or plant cell is a monocotyledon plant or plant cell.

12. A seed of the transgenic plant of claim 9, wherein the seed comprises the DNA construct.

13. A method for expressing a polynucleotide in a plant, said method comprising introducing into a plant cell a recombinant heterologous polynucleotide, said recombinant heterologous polynucleotide comprising a regulatory element operably linked to a heterologous transcribable polynucleotide molecule, wherein said regulatory element is selected from the group consisting of:
   a. a nucleotide sequence comprising the nucleotide sequence set forth in SEQ ID NO: 12;
   b. a nucleotide sequence that is at least 95% identical to SEQ ID NO: 12 having regulatory activity; or
   c. a nucleotide sequence comprising a functional fragment of at least 100 contiguous nucleotides of the nucleotide sequence of SEQ ID NOs: 12, wherein the nucleotide sequence has regulatory activity in a plant cell.

14. The method of claim 13, wherein the heterologous polynucleotide encodes a gene product that is involved in organ development, stem cell development, cell growth stimulation, organogenesis, somatic embryogenesis initiation and development of the apical meristem.

15. The method of claim 13, wherein said heterologous polynucleotide is an endogenous gene of the plant.

16. The method of claim 13, wherein the heterologous polynucleotide encodes a gene product that confers drought tolerance, cold tolerance, herbicide tolerance, pathogen resistance, or insect resistance.

17. The method of claim 13, wherein said plant is a dicot.

18. The method of claim 13, wherein said plant is a monocot.

\* \* \* \* \*

SEQUENCE LISTING

```
<160> NUMBER OF SEQ ID NOS: 14

<210> SEQ ID NO 1
<211> LENGTH: 187
<212> TYPE: DNA
<213> ORGANISM: Mirabilis Mosaic Virus

<400> SEQUENCE: 1
ccactaaaac attgctttgt caaaagctaa aaaagatgat gcccgacagc cacttgtgtg      60
aagcatgaga agccggtccc tccactaaga aaattagtga agcatcttcc agtggtccct     120
ccactcacag ctcaatcagt gagcaacagg acgaaggaaa tgacgtaagc catgacgtct     180
aatccca                                                              187

<210> SEQ ID NO 2
<211> LENGTH: 384
<212> TYPE: DNA
<213> ORGANISM: Artificial Sequence
<220> FEATURE:
<223> OTHER INFORMATION: synthetic

<400> SEQUENCE: 2
ccactaaaac attgctttgt caaaagctaa aaaagatgat gcccgacagc cacttgtgtg      60
aagcatgaga agccggtccc tccactaaga aaattagtga agcatcttcc agtggtccct     120
ccactcacag ctcaatcagt gagcaacagg acgaaggaaa tgacgtaagc catgacgtct     180
aatcccactc gatcgaccca ctaaaacatt gctttgtcaa aagctaaaaa agatgatgcc     240
```

```
cgacagccac ttgtgtgaag catgagaagc cggtccctcc actaagaaaa ttagtgaagc      300
atcttccagt ggtccctcca ctcacagctc aatcagtgag caacaggacg aaggaaatga      360
cgtaagccat gacgtctaat ccca                                              384

<210> SEQ ID NO 3
<211> LENGTH: 573
<212> TYPE: DNA
<213> ORGANISM: Artificial Sequence
<220> FEATURE:
<223> OTHER INFORMATION: synthetic

<400> SEQUENCE: 3
ccactaaaac attgctttgt caaaagctaa aaagatgat gcccgacagc cacttgtgtg        60
aagcatgaga agccggtccc tccactaaga aaattagtga agcatcttcc agtggtccct      120
ccactcacag ctcaatcagt gagcaacagg acgaaggaaa tgacgtaagc catgacgtct      180
aatcccactc gagccactaa acattgctt tgtcaaaagc taaaaaagat gatgcccgac       240
agccacttgt gtgaagcatg agaagccggt ccctccacta gaaaattag tgaagcatct      300 tccagtggtc cctccactca gctcaatc agtgagcaac aggacgaagg aaatgacgta       360
agccatgacg tctaatccca gtcgaccac taaaacattg ctttgtcaaa agctaaaaaa      420
gatgatgccc gacagccact tgtgtgaagc atgagaagcc ggtccctcca ctaagaaaat      480
tagtgaagca tcttccagtg gtccctccac tcacagctca atcagtgagc aacaggacga      540
aggaaatgac gtaagccatg acgtctaatc cca                                    573

<210> SEQ ID NO 4
<211> LENGTH: 259
<212> TYPE: DNA
<213> ORGANISM: Bean Yellow Dwarf Virus

<400> SEQUENCE: 4
tgtgaacacc tttaaccta gtgggcggga acttttctac tttaaatctg gaccgctcgt       60
gctaaagcac tcgcgataag gtggggccac gccggtaata ttaaaattcg gcgtgggccc     120
cccttgtcgc aagacttcgt ctttaagtaa atgacgtcat tttccactaa ctacttaaat     180
taccaaaatg cccttgcctc catgcctcca cgccggttat aagatagagt ttgaggcaac     240
ccctcggagt cacaacaac                                                    259

<210> SEQ ID NO 5
<211> LENGTH: 310
<212> TYPE: DNA
<213> ORGANISM: Beet Mild Curly Top Virus

<400> SEQUENCE: 5
gtagaaataa attcgaaact tacacagcaa gttttgaata gtaacaattc ctttacttta      60
caaaagtaaa aatatttgtc ggccacaact tttgactagt caaaacttat aagagaagga    120
aacttcctat gtaagtttcc aagtaccgac aactatataat gcgattacac gtgtcacgtt    180
tcaaatggga gggaaaaatt ttcggggcca tccggtaata ttattgcgga tggcccctgg    240
tggtatataa gggctcccat agcaccccat tcatacaagt ttacgagagc ccccaatagg    300
aatagtaacc                                                              310

<210> SEQ ID NO 6
<211> LENGTH: 346
<212> TYPE: DNA
<213> ORGANISM: East African Cassava Mosaic (Cameroon) Virus
```

<400> SEQUENCE: 6

```
ctaacgggat tccacatttt gacgcgcttc actacttcgt gacgaagtat ttaaagtcaa      60
aactcaatat ctagcattca aggcgcaact attattggcc gacaaacatg cgtgcgcggg     120
gaccactttc ttttgcggac gcggactatc atggggccca cctgctttt tcgggcgcgg     180 ccatccggta atattaatcg gatggccgcc aatattcgca attcaaattt tgaatggaag     240
tctacctatt tacacatatg ccattggggg acatcatata tattgccccc cattccaccg     300
ttcccctgga gttttgagtg tccccgata caaaacgaca gccaat                    346
```

<210> SEQ ID NO 7
<211> LENGTH: 251
<212> TYPE: DNA
<213> ORGANISM: Hollyhock leaf crumple virus

<400> SEQUENCE: 7

```
tttcaaattt caaattataa tgcgtacagc gcgcgttttg attggacagc aacgcgcgac      60
atgttcacgt ggcggggacc acttttttt ttcgcgccca ccggtaatat tagaacggtg     120
ggcgctatgg gggttcaaaa ttattgggat ttttaccaaa atgccatttg gtgtacaact     180
atatattgta ccccattaca ccgattgcag gcaccaaatg aaatccaagt caatcggtgt     240
acattgacca a                                                         251
```

<210> SEQ ID NO 8
<211> LENGTH: 287
<212> TYPE: DNA
<213> ORGANISM: Horseradish Curly Top Virus

<400> SEQUENCE: 8

```
tttgtacata tataaatata tgtacaaata ccgtatttat ttaaaaggat aaagttaaac      60
ttgccgacca agtttcctag tggggtctac tttactttac tttataaaac cggtcgccgc     120
cacttttgac cagccaacaa ttttaagaca cgtggtagca tcgcggccat ccgtaatat     180 tagaacggat ggccgctatt ggccttaaga ggttttagta taaatgagac tccagaactc     240
cacgaatatg acaggattaa acctaaaacc tggagtccca gttcaaa                  287
```

<210> SEQ ID NO 9
<211> LENGTH: 298
<212> TYPE: DNA
<213> ORGANISM: Macroptilium Yellow Mosaic Florida Virus

<400> SEQUENCE: 9

```
ggaaatttgg caacttggtg accaagttgc gacaaattaa atagacaatg cacgaacaaa      60
ttgattggtc agtcaaaaat ccttatcttt aatttaaatt aaagcgtcac gtgggtgtgt     120
acggaaagtg gggggcggg gcgcggccat ccggtaatat tatttcggat ggccgccacg     180
tgtgcgaacg agattgaggg ttctattgag ggttctagta tttatagtac ccctttacac     240
caattgatag agcaagtttg agagagctca ttcggggtac actctcatat tttccaaa      298
```

<210> SEQ ID NO 10
<211> LENGTH: 249
<212> TYPE: DNA
<213> ORGANISM: Sugarcane Streak (Egypt) Virus

<400> SEQUENCE: 10

```
cgatccaaag cgccttacta catacaggct ttaacgaaag acatagggcc ccaaagcggg      60
```

```
accgctcggc ctggtgggcc tcgcatgaga gagcgcggta atattatcgg tttgcgctct      120
ctcattgcgg cccaggaaaa atcctggccc ggcccaacta accttctata aagacgggga      180
ggtcggattt cgattcgcaa acctgtagga gagttagttg agactcagaa tcagacctct      240
cgcccagcc                                                              249

<210> SEQ ID NO 11
<211> LENGTH: 257
<212> TYPE: DNA
<213> ORGANISM: Sugarcane Streak Virus

<400> SEQUENCE: 11
tgcgatccaa agccggcgtt tcaaagcagc cggcaataaa gaacaaaacg cacccagaac      60
cgggacccgt cggcctggtg ggcctcgcat gaaaaagcgc tgtaatatta ttggtttgcg      120 cttttttcatt gcggcccaag aaaaaattcg gcccagccca tttagcactc ctataagagg    180
gcagggggag tcgtgattc taaatcgcaa acctgtagga ggttggttga ggctccaaat      240
cagacactgc ccaaaga                                                    257

<210> SEQ ID NO 12
<211> LENGTH: 256
<212> TYPE: DNA
<213> ORGANISM: Tomato Curly Stunt Virus (South Africa)

<400> SEQUENCE: 12
aagacaaaat agcagataac taagcgataa ggcgacattc tgattggtcg acataaaata     60
gtgcgtgggg accactttt tttgggggca cggccatccg gtaatattaa tcggatggcc      120
gctttgggag tttgaatttt gaaataccaa ttaatttcac acaaattaca attgtgccat      180
tcagtaccca ctatatattg ggtaccgata taccaggaga atgcaatttg agagtcaatc     240
ggtaccattt gaccaa                                                    256

<210> SEQ ID NO 13
<211> LENGTH: 378
<212> TYPE: DNA
<213> ORGANISM: Wheat Dwarf Virus

<400> SEQUENCE: 13
ctaaggcatg gcacagattt ccaagtcaaa agtgtgataa atcaacatct tccacgaaag      60
tgatcagaaa agatgtggtc caaaagcctc cgcgcactca cgaaaagccg agtgcgcgtc     120
gggggccacc acgcggggta atattataac ccgcgtggag gccccccgac acacaccga     180 acagggccca cacgatacgc tacgctcccg tgggaacaca agggccctgt tctcccgcca     240
aaacctgccc tatataaagc attggacaca ttgcatttgc agtgtgcaga attcacacct     300
ccacgcaggg tagagcatag agttttctgg cacacccgt tttttcgcta aggacctgcc      360
ggacttctgt tcactacc                                                  378

<210> SEQ ID NO 14
<211> LENGTH: 1710
<212> TYPE: DNA
<213> ORGANISM: Sorghum bicolor

<400> SEQUENCE: 14
ttttaagtat gaccaatttt taagtataaa cccctcacga ttggttattt ttttaagtat     60
aaccaatttt taagtataaa cccctcacca atttttaagt ataaacctag cgactaataa    120
acacaacttc ttgccaaagt gtgagcatca ccattggatc tgcgcccctc acgaacagtc    180
```

```
ttcgccgggg taaaattctc caaattaaag tcatcttgat gtccttgatc acctgtccat    240
aaggcccaat cccagctcca cgtatacttc tgataagatt gacatagtca cttgcatgcc    300
agtgtggaac tctggatgcc taggtcagag gctagtgact ggccttcccg gcatgctagc    360
atgtagcatg ccaaggatct ggctgctcca ggtttgttat gcctgacatc accatagggga   420 tgagagcaag tataataata ggctgtaagc tttaaatgct caggtggaga aaaaaggag     480 aggagaggag agagaaaagt gggctataag cttatagctg tgttagacat aagaatcaga    540
aacttcgtat gagagacagg tgagctatat attaataaca aagagctaac tattatatga    600
gtgaaccgag agaaggctgt aaaaaaactt acacaatcaa cgatcgacat tattattaac    660
cttgctctgt cttgcgagac ctctttgaca aagctacatc aatgccggcc aagtgccttg    720
ggatttggga atggcttctt tcctcccttc ctcggttgtc ccccaaggcc taggcttgcc    780
acgctgtatt cagtcgcagc cgcctttact tttgcccttt gtggaagttt tgtaataaat    840
ggtctgattc tatcttcgga tagatgaagc cggatgtttc atccattatc taaaaaaaag   900
ttggttgctt tgctgagcta agaaagtgta atccagagtg ctcgtaacgt attaatgtac    960
ataactatta tctaatataa atcttctttt gtcgcaaaaa aaggtcggcc catcagaaca   1020
aatgatcaat gtaaggccca aaatttgtgt ctcaaatgtc atttacgttt ccaagctaaa   1080
caaaaacaca ggattcatat aattttgctg gtggcttagg cttcgtccaa tagtgcttag   1140
tttaatttgt atatacctgc accatggtat tcgtctggcc ttggatcttg cgcatcaatt   1200
gcctatggac gatgatcgca gccacgccac attcattttt aatcgccatt tgcttgacac   1260
ccaatgcctc tgcaccactt gcgcacgcta cgcaccgtct gatacgccaa gatcccgagc   1320
taaaataaca cccaatcatc agatgaaaac aagcgcgagt gcgagccagc ccatggcagc   1380
gatcttggcc atttgcggag ccaactgaaa gccgtgcaca aaatattcga caccgtataa   1440
gggaaaacac tagttatacg aggtgggcaa taatccagat ctcggactct tcctaacccg   1500
gttcacatgc atagcatata tgatggccgg ccggggttca catgaacgcc atcccgtgcc   1560
ctagtgcact gatttcttaa tcccgggtct caactataaa taccccccttg gtgacaccgc  1620 gatcaaagca tcgcaaacaa gcctagctaa gagctctcta actacattag atagagtgat   1680
ctcgagaggt aactggcttg tgatcgagca                                    1710
```